United States Patent
Park et al.

(10) Patent No.: US 6,610,733 B2
(45) Date of Patent: Aug. 26, 2003

(54) OPTICALLY ACTIVE CHROMAN AND THIOCHROMAN DERIVATIVES

(75) Inventors: SungDae Park, Seoul (KR); HeeAn Kwon, Kyonggi-do (KR); HongKi Kim, Kyonggi-do (KR); PilSu Ho, Kyonggi-do (KR); Kazumi Morikawa, Shizuoka (JP); Yoshitake Kanbe, Shizuoka (JP); Masahiro Nishimoto, Shizuoka (JP); MyungHwa Kim, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/149,748

(22) PCT Filed: Dec. 13, 2000

(86) PCT No.: PCT/JP00/08807

§ 371 (c)(1),
(2), (4) Date: Jun. 13, 2002

(87) PCT Pub. No.: WO01/42233

PCT Pub. Date: Jun. 14, 2001

(65) Prior Publication Data

US 2003/0125571 A1 Jul. 3, 2003

(30) Foreign Application Priority Data

Dec. 13, 1999 (JP) ............................................ 11-353413

(51) Int. Cl.[7] ................... A61K 31/385; A61K 31/355; C07D 335/04; C07D 311/04
(52) U.S. Cl. .................... 514/434; 514/458; 549/23; 549/406
(58) Field of Search ................. 514/434, 458; 549/23, 406

(56) References Cited

U.S. PATENT DOCUMENTS

| | | | |
|---|---|---|---|
| 6,153,768 A | * 11/2000 | Jo et al. ................. | 549/406 |
| 6,316,494 B1 | * 11/2001 | Jacobsen et al. ............. | 514/456 |
| 6,342,602 B1 | * 1/2002 | Teng et al. .................. | 544/238 |
| 6,387,882 B1 | * 5/2002 | Ogata et al. .................. | 514/18 |
| 6,417,223 B1 | * 7/2002 | Saunders et al. ............. | 514/456 |
| 6,495,524 B1 | * 12/2002 | Hattori et al. ................. | 514/27 |

FOREIGN PATENT DOCUMENTS

WO    WO 99/65893 A1    12/1999

* cited by examiner

Primary Examiner—Deborah C. Lambkin
(74) Attorney, Agent, or Firm—Browdy and Neimark, P.L.L.C.

(57) ABSTRACT

The present invention includes a compound having the following general formula (1):

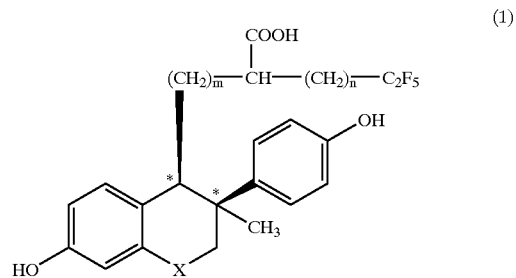

in which x represents an oxygen atom or a sulfur atom, m represents an integer of 2 to 14, and n represents an integer of 2 to 7, or hydrates or pharmaceutically acceptable salts thereof. The compound of general formula (1) is advantageous in pharmaceutical use because of its far superior anti-estrogenic activity over the corresponding racemic mixture.

13 Claims, No Drawings

OPTICALLY ACTIVE CHROMAN AND THIOCHROMAN DERIVATIVES

This application is a 371 of PCT/JP00/08801 Dec. 13, 2000.

TECHNICAL FIELD

The present invention relates to optically active chroman or thiochroman derivatives having anti-estrogenic activity.

BACKGROUND ART

In treating diseases caused by abnormal tissue growth that is dependent upon a certain sexual steroidal hormone such as estrogen, it is highly important to significantly inhibit, more preferably completely eliminate, the effect induced by the hormone. For this purpose, it is desirable to reduce the level of hormone capable of acting on the steroidal hormone receptor site. For instance, anti-estrogenic agents are commonly administered for alternative or combination therapy to limit the production of estrogen to the amount less than required to activate the receptor site. However, such conventional technique for blocking estrogen production could not sufficiently inhibit the effect induced through the estrogen receptor. Practically, even when estrogen is completely absent, some of the receptors may be activated. It was therefore considered that estrogen antagonists could provide better therapeutic effect in comparison to the technique for blocking only the production of sexual steroidal hormone. Thus, numerous estrogen antagonists have been developed. For example, many patent publications including U.S. Pat. Nos. 4,760,061, 4,732,912, 4,904,661, 5,395,842 and WO 96/22092 disclose various anti-estrogenic compounds. Sometimes, however, prior art antagonists may themselves act as agonists, and therefore activate rather than block the receptor. For example, Tamoxifen has been most widely used as an anti-estrogenic agent. However, this agent has a disadvantage that it exhibits estrogenic activity in some organs (see, M. Harper and A. Walpole, J. Reprod. Fertile., 1967, 13, 101).

As another non-steroidal anti-estrogenic compound, WO 93/10741 discloses a benzopyran derivative having an aminoethoxyphenyl substituent(s) (Endorecherche), the typical compound of which is EM-343 having the following structure:

EM-343

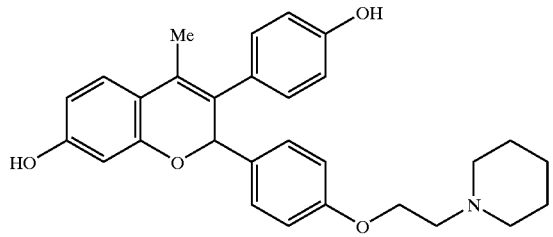

Said compound also has the agonistic effect. It is therefore required to develop an anti-estrogenic compound which is substantially or completely free of agonistic effect and which can effectively block the estrogen receptor.

In addition, it has been known that 7α-substituted derivatives of estradiol, for example, 7α-$(CH_2)_{10}$CONMeBu derivatives, are steroidal anti-estrogenic agents without agonistic effect (see, EP-A 0138504, U.S. Pat. No. 4,659,516). Further, an estradiol derivative having a 7α-$(CH_2)_9$SO$C_5H_6F_5$ substituent has also been disclosed (see, Wakeling et al., Cancer Res., 1991, 51, 3867).

Non-steroidal anti-estrogenic agents without agonistic effect have been first reported by Wakeling et al. in 1987 (see, A. Wakeling and Bowler, J. Endocrinol., 1987, 112, R7). Meanwhile, U.S. Pat. No. 4,904,661 discloses phenol derivatives having anti-estrogenic activity. These phenol derivatives generally have a naphthalene scaffold and include, typically, the following compounds:

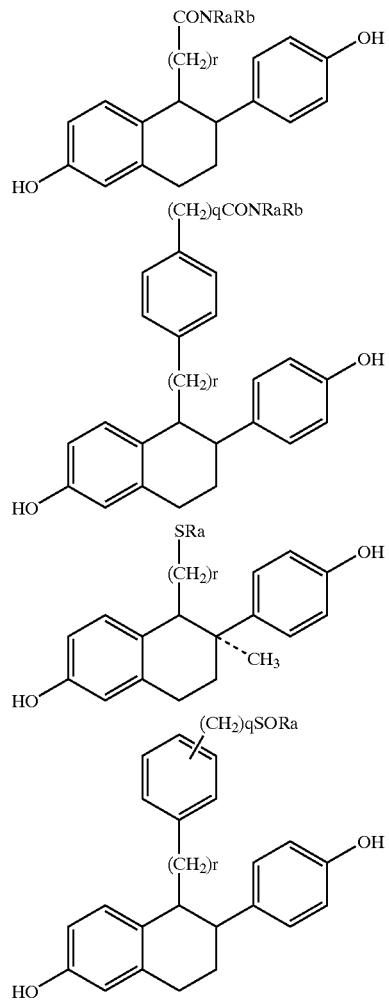

Some chroman and thiochroman derivatives have been reported as anti-estrogenic compounds having no agonistic effect (WO 98/25916). Although the existing anti-estrogenic compounds having no agonistic effect show a substantial therapeutic effect when administered via intravenous or subcutaneous injection, they show a highly reduced therapeutic effect when administered orally, probably due to their low bioavailability by oral route, etc. Therefore, for convenience's sake in the case of administration, it is desired to develop anti-estrogenic compounds which show a sufficient effect when administered orally and at the same time have no agonistic effect.

DISCLOSURE OF THE INVENTION

The object of the present invention is to provide optically active chroman or thiochroman derivatives with asymmetric center(s), which have an excellent anti-estrogenic activity and are advantageous in pharmaceutical use.

The present inventors have researched anti-estrogenic activity of compounds having various structures. As a result, we have found that optically active chroman or thiochroman derivatives represented by general formulae (1) to (4) could be more advantageous in pharmaceutical use because of, for example, their far superior anti-estrogenic activity over the corresponding diastereomer mixture. The present invention has been accomplished on the basis of this finding.

Namely, the present invention provides a compound having the following general formula (1):

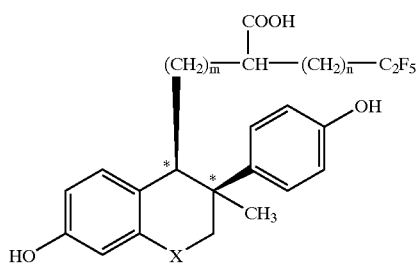

(1)

in which x represents an oxygen atom or a sulfur atom, m represents an integer of 2 to 14, and n represents an integer of 2 to 7, or the following general formula (2):

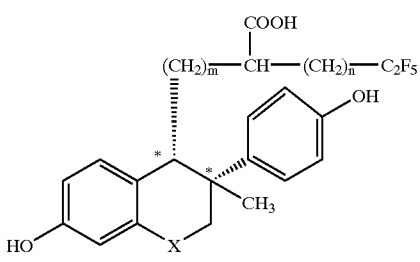

(2)

in which x represents an oxygen atom or a sulfur atom, m represents an integer of 2 to 14, and n represents an integer of 2 to 7, or the following general formula (3):

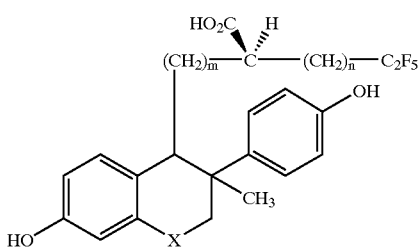

(3)

in which x represents an oxygen atom or a sulfur atom, m represents an integer of 2 to 14, and n represents an integer of 2 to 7, or the following general formula (4):

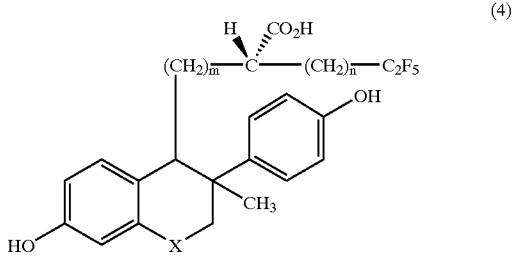

(4)

in which x represents an oxygen atom or a sulfur atom, m represents an integer of 2 to 14, and n represents an integer of 2 to 7, or hydrates thereof.

In addition, the present invention provides an optically single isomer of a compound having general formula (1) or (2) where the carbon which is on the side chain bonded to the 4-position of the parent scaffold (i.e., chroman or thiochroman ring) and to which the carboxylic acid in said side chain is bonded has R- or S-configuration, and mixtures thereof.

Further, the present invention provides a pharmaceutical composition comprising an optically active compound of general formula (1), (2), (3) or (4) as an active ingredient. Furthermore, the present invention provides an anti-estrogenic pharmaceutical composition comprising the above compound as an active ingredient. The present invention also provides a therapeutic agent for breast cancer comprising the above compound as an active ingredient.

In the definition of a compound having general formula (1), (2), (3) or (4), m may preferably be an integer of 6 to 10, particularly 8 or 9, and n may preferably be an integer of 2 to 7, particularly 3 or 4.

Compounds of general formula (1) or (2) have chiral carbons at positions 3 and 4 of the parent scaffold (i.e., chroman or thiochroman ring) in either the (3S,4S) or (3R,4R) configuration. Any of these compounds is preferred per se. In particular, the compounds having R- or S-configuration at the carbon to which the carboxylic acid is bonded are more preferable, wherein said carbon is the carbon on the side chain which is bonded to the 4-position of the parent scaffold. Also preferred are compounds of general formula (2), particularly those compounds in which X is a sulfur atom.

Another aspect of the present invention includes compounds of general formula (1) or (2) in which X is an oxygen atom.

Among compounds of general formula (1) or (2), preferred are those compounds in which X is an oxygen atom or a sulfur atom; m is an integer of 8 or 9; and n is an integer of 3 or 4. In particular, the compound having R- or S-configuration at the carbon to which the carboxylic acid is bonded are more preferable, wherein said carbon is the carbon on the side chain which is bonded to the 4-position of the parent scaffold.

As typical examples of these compounds, the following compounds can be mentioned:

10-[(3R,4R)-7-hydroxy-3-(4-hydroxyphenyl)-3-methylthiochroman-4-yl]-(2R)-2-(4,4,5,5,5-pentafluoropentyl)decanoic acid;

10-[(3R,4R)-7-hydroxy-3-(4-hydroxyphenyl)-3-methylthiochroman-4-yl]-(2S)-2-(4,4,5,5,5-pentafluoropentyl)decanoic acid;

10-[(3S,4S)-7-hydroxy-3-(4-hydroxyphenyl)-3-methylthiochroman-4-yl]-(2R)-2-(4,4,5,5,5-pentafluoropentyl)decanoic acid;

10-[(3S,4S)-7-hydroxy-3-(4-hydroxyphenyl)-3-methylthiochroman-4-yl]-(2S)-2-(4,4,5,5,5-pentafluoropentyl)decanoic acid;

10-[(3R,4R)-7-hydroxy-3-(4-hydroxyphenyl)-3-methylthiochroman-4-yl]-2-(4,4,5,5,5-pentafluoropentyl)decanoic acid;

10-[(3S,4S)-7-hydroxy-3-(4-hydroxyphenyl)-3-methylthiochroman-4-yl]-2-(4,4,5,5,5-pentafluoropentyl)decanoic acid;

10-[(3RS,4RS)-7-hydroxy-3-(4-hydroxyphenyl)-3-methylthiochroman-4-yl]-(2R)-2-(4,4,5,5,5-pentafluoropentyl)decanoic acid;

10-[(3RS,4RS)-7-hydroxy-3-(4-hydroxyphenyl)-3-methylthiochroman-4-yl]-(2S)-2-(4,4,5,5,5-pentafluoropentyl)decanoic acid;

11-[(3R,4R)-7-hydroxy-3-(4-hydroxyphenyl)-3-methylthiochroman-4-yl]-(2R)-2-(4,4,5,5,5-pentafluoropentyl)undecanoic acid;

11-[(3R,4R)-7-hydroxy-3-(4-hydroxyphenyl)-3-methylthiochroman-4-yl]-(2S)-2-(4,4,5,5,5-pentafluoropentyl)undecanoic acid;

11-[(3S,4S)-7-hydroxy-3-(4-hydroxyphenyl)-3-methylthiochroman-4-yl]-(2R)-2-(4,4,5,5,5-pentafluoropentyl)undecanoic acid;

11-[(3S,4S)-7-hydroxy-3-(4-hydroxyphenyl)-3-methylthiochroman-4-yl]-(2S)-2-(4,4,5,5,5-pentafluoropentyl)undecanoic acid;

11-[(3R,4R)-7-hydroxy-3-(4-hydroxyphenyl)-3-methylthiochroman-4-yl]-2-(4,4,5,5,5-pentafluoropentyl)undecanoic acid;

11-[(3S,4S)-7-hydroxy-3-(4-hydroxyphenyl)-3-methylthiochroman-4-yl]-2-(4,4,5,5,5-pentafluoropentyl)undecanoic acid;

11-[(3RS,4RS)-7-hydroxy-3-(4-hydroxyphenyl)-3-methylthiochroman-4-yl]-(2R)-2-(4,4,5,5,5-pentafluoropentyl)undecanoic acid; and 11-[(3RS,4RS)-7-hydroxy-3-(4-hydroxyphenyl)-3-methylthiochroman-4-yl]-(2S)-2-(4,4,5,5,5-pentafluoropentyl)undecanoic acid.

The compounds of the present invention may be obtained as hydrates.

The compound of general formula (1), (2), (3) or (4) may be administered as a pharmaceutical composition in any dosage form suitable for the intended route of administration, in combination with one or more pharmaceutically acceptable diluents, wetting agents, emulsifiers, dispersants, auxiliary agents, preservatives, buffers, binders, stabilizers and the like. The compound and composition may be administered parenterally or orally.

The dose of the compound can be suitably determined according to the physique, age and physical condition of a patient, severity of the disease to be treated, elapsed time after onset of the disease, etc. Because the compound of the present invention is expected to show a higher therapeutic effect than the corresponding diastereomer mixture, it may be used in a smaller amount to achieve the same level of therapeutic effect. For example, it is generally used in an amount of 0.1 to 500 mg/day when orally administered and in an amount of 1 to 1000 mg/month when parenterally administered (by intravenous, intramuscular, or subcutaneous route) for adult patient.

BEST MODE FOR CARRYING OUT THE INVENTION

The compound of general formula (1) or (2) can be prepared according to any one of the following Reaction Schemes 1 to 10 (Processes 1 to 10). In these Reaction Schemes 1 to 10, compounds marked with an asterisk (*), for example, compound (I*) based on compound (I), are defined as follows:

(a) compounds (III*), (IV*), (XIII*), (XIV*), (XIX*), (XX*), (XXII*), (XXIV*), (XXXI*) and (XXXIV*): each carbon atom marked with an asterisk in these chemical structures shown in the reaction schemes takes a single configuration; and (b) compounds marked with an asterisk other than those defined above in (a): these compounds are in an optically active form.

The compound of general formula (3) or (4) can be prepared according to any one of the following Reaction Schemes 1 to 10 (Processes 1 to 10), starting with racemate (I) (Reaction Schemes 1 and 6), racemate (XII) (Reaction Scheme 2), racemate (VII) (Reaction Scheme 3), racemate (XVII) (Reaction Schemes 4 and 5), XXV (Reaction Scheme 7), racemate (XXIX) (Reaction Schemes 8 and 9), or optically active compounds (XXXV*) and (XXXVI*) (Reaction Scheme 10).

Reaction Scheme 1 (Process 1)

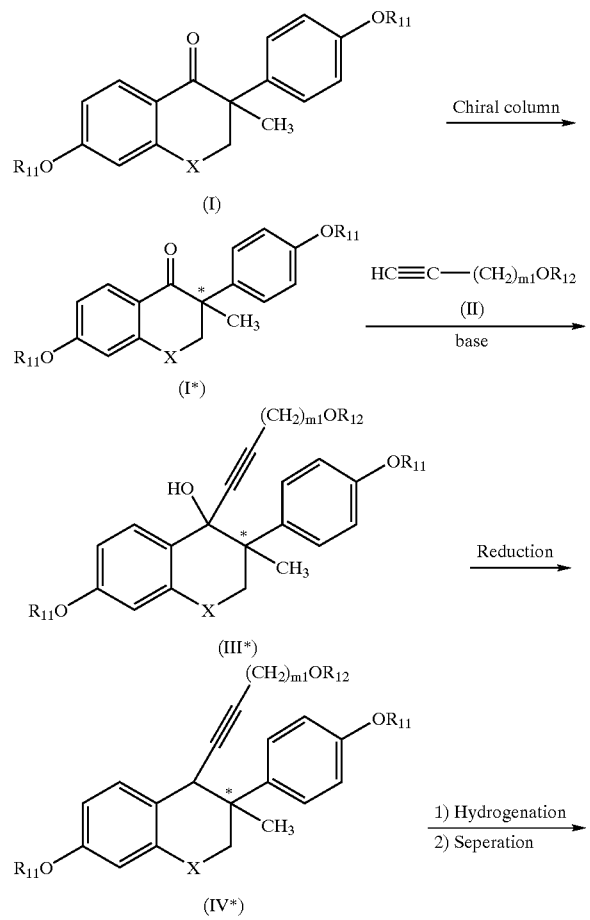

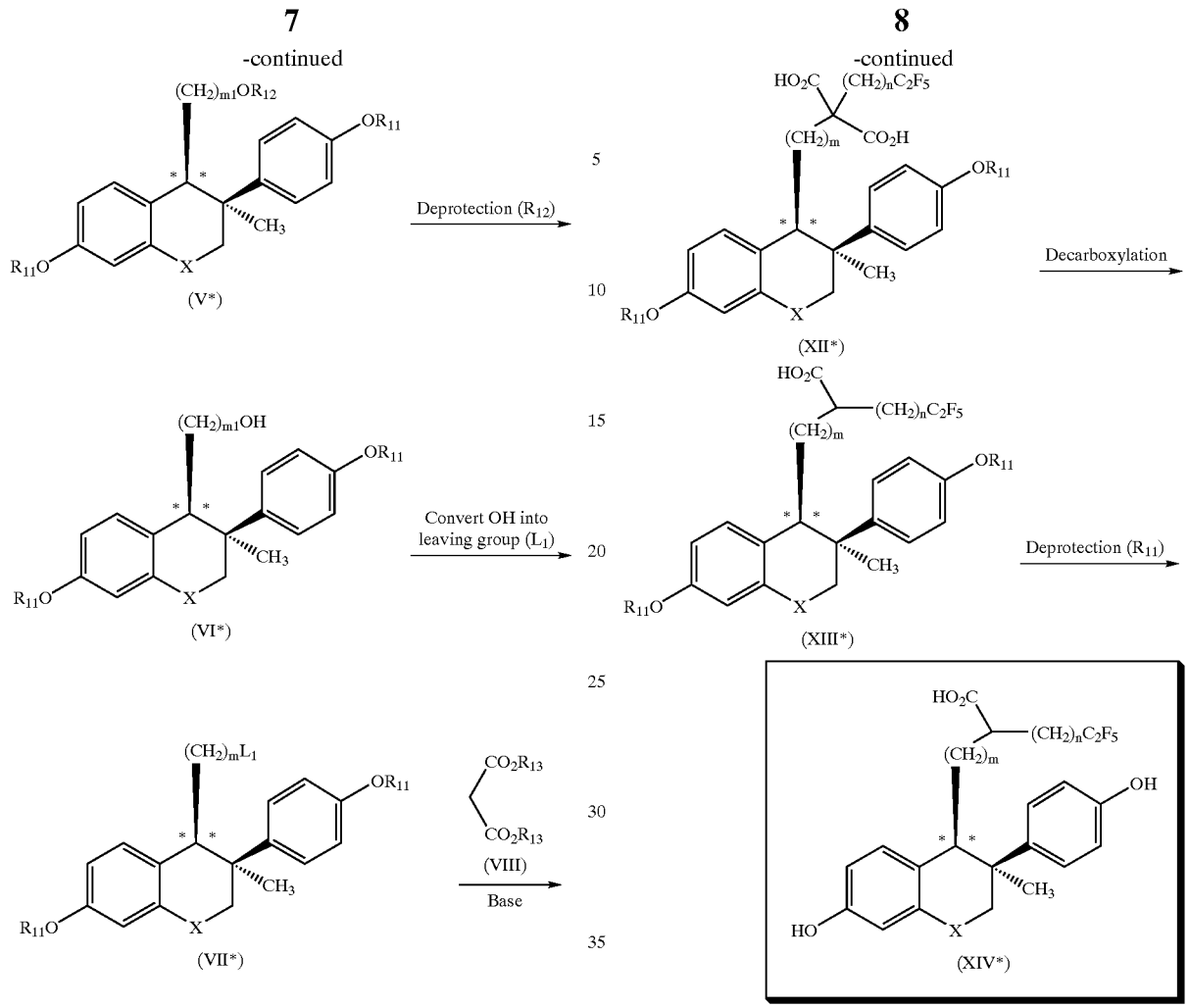
In the above Reaction Scheme 1 (Process 1), X, m and n are as defined above in general formulae (1) to (4); each of $R_{11}$, $R_{12}$ and $R_{13}$ represents a protecting group; each of $L_1$ and $L_2$ represents a leaving group; and $m_1$ equals $m-2$.
Reaction Scheme 2 (Process 2)
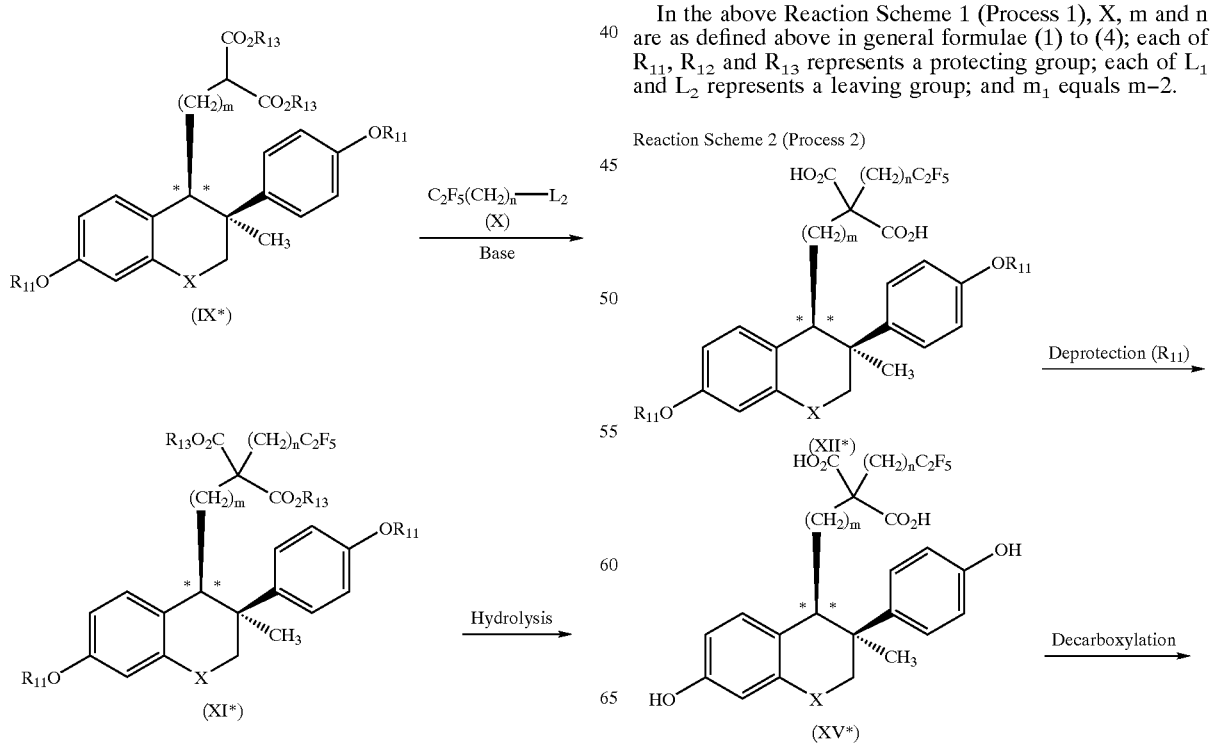

-continued

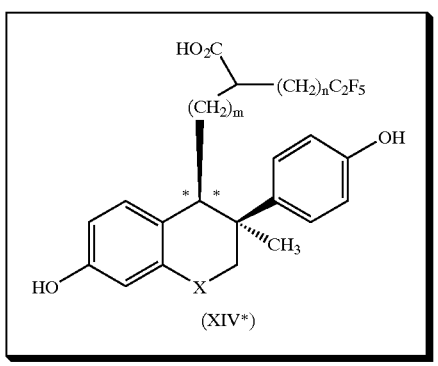

In the above Reaction Scheme 2 (Process 2), X, m and n are as defined above in general formulae (1) to (4); and $R_{11}$ represents a protecting group.

Reaction Scheme 3 (Process 3)

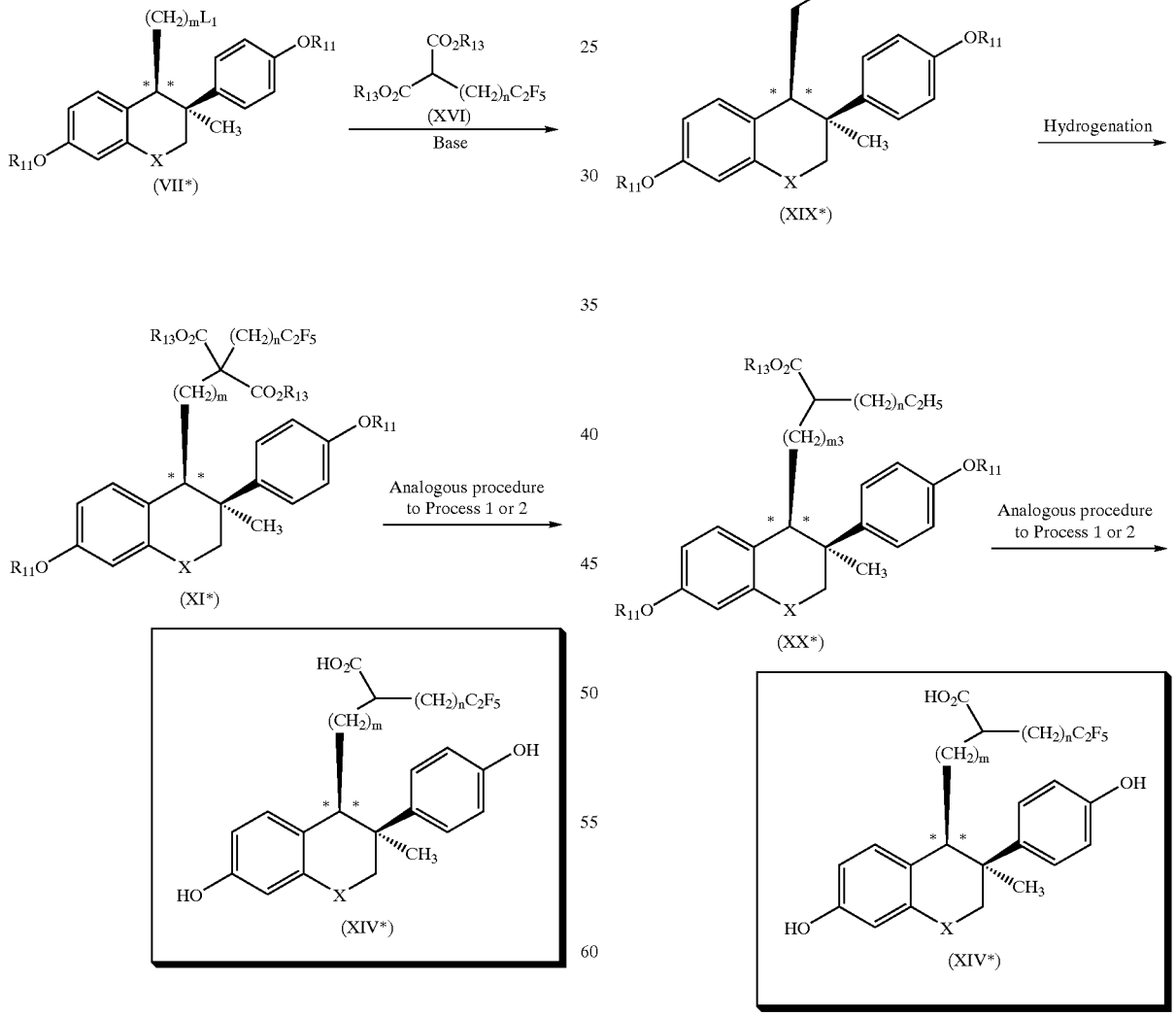

In the above Reaction Scheme 3 (Process 3), X, m and n are as defined above in general formulae (1) to (4); each of $R_{11}$ and $R_{13}$ represents a protecting group; and $L_1$ represents a leaving group.

Reaction Scheme 4 (Process 4)

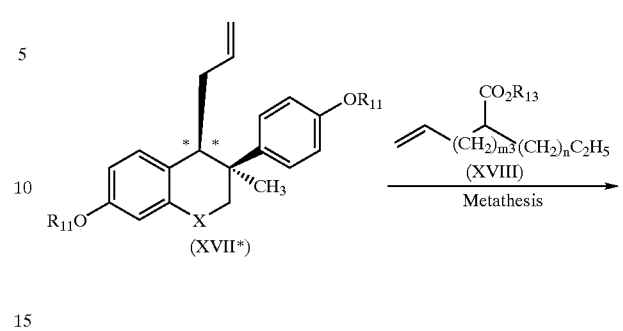

In the Reaction Scheme 4 (Process 4), X, m and n are as defined above in general formulae (1) to (4); each of $R_{11}$ and $R_{13}$ represents a protecting group; and $m_3+3$ equals m.

Reaction Scheme 5 (Process 5)

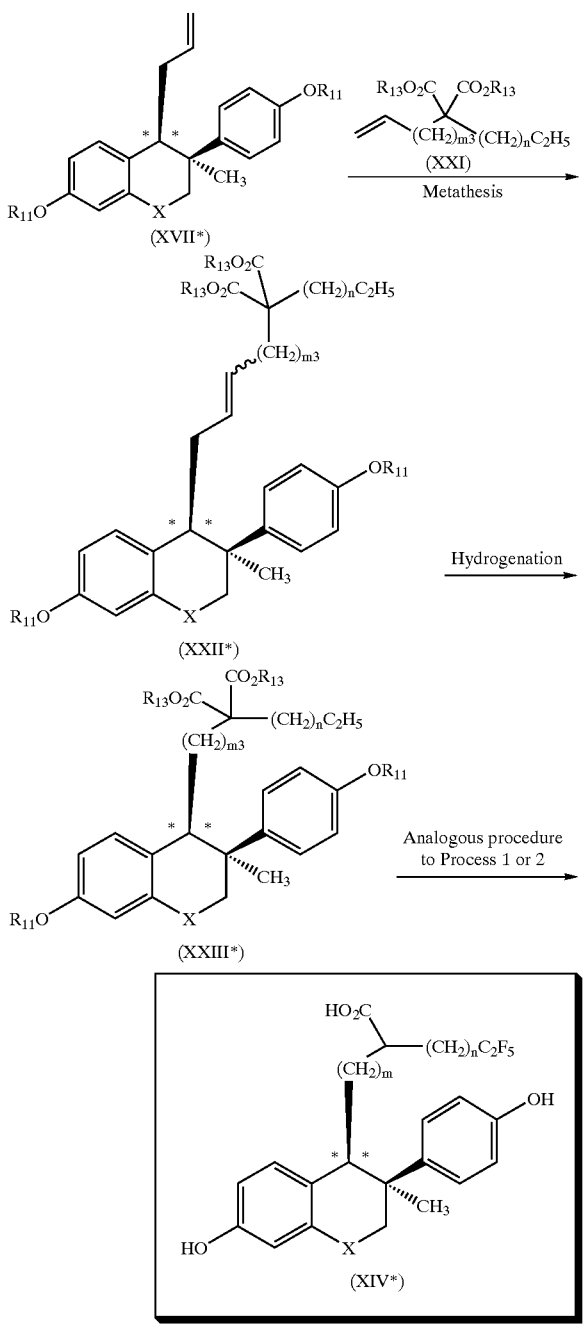

In the above Reaction Scheme 5 (Process 5), X, m and n are as defined above in general formulae (1) to (4); each of $R_{11}$ and $R_{13}$ represents a protecting group; and $m_3+3$ equals m.

The preparation of the compounds according to the present invention will be illustrated below in more detail, in line with the above-mentioned reaction schemes.

[Process 1]

Racemate (I) is resolved using a chiral column, for example, one commercially available from DAICEL under the trade name of CHIRALPAK-OT(+), OP(+) or AD, or CHIRALCEL-OA, OB, OJ, OK, OC, OD, OF or OG, to give optically active compound (I*).

In the presence of a base (e.g., n-butyllithium, s-butyllithium, sodium hydride), compound (I*) is reacted with alkyne (II) in an inert solvent (e.g., tetrahydrofuran, diethyl ether, dioxane, dichloromethane, chloroform, preferably tetrahydrofuran or dioxane) at a temperature ranging from −78° C. to the boiling point of the reaction mixture, preferably from −78° C. to room temperature, to give compound (III*).

In the presence of a Lewis acid such as zinc iodide, compound (III*) is reduced with sodium cyanoborohydride ($NaBH_3CN$) in an inert solvent (e.g., tetrahydrofuran, diethyl ether, dioxane, dichloromethane, dichloroethane or chloroform, preferably dichloroethane) at a temperature ranging from −78° C. to the boiling point of the reaction mixture, preferably from 0° C. to room temperature, to give compound (IV*).

Using a catalyst (e.g., palladium on activated carbon, palladium hydroxide, platinum oxide), compound (IV*) is hydrogenated in an inert solvent (e.g., methanol, ethanol, ethyl acetate, tetrahydrofuran, dioxane, preferably tetrahydrofuran, ethyl acetate) at a temperature ranging from room temperature to the boiling point of the reaction mixture, preferably at room temperature, to give compound (V*). Compound (V*) can be directly prepared from compound (III*) through hydrogenation using a catalyst (e.g., palladium on activated carbon, palladium hydroxide or platinum oxide) in an inert solvent (e.g., methanol, ethanol, ethyl acetate, tetrahydrofuran, dioxane, preferably tetrahydrofuran, ethyl acetate) at a temperature ranging from room temperature to the boiling point of the reaction mixture, preferably at room temperature.

Compound (V*) is subjected to deprotection of the alcoholic hydroxyl group in an inert solvent to give compound (VI*).

In the presence of a base (e.g., triethylamine or pyridine), compound (VI*) is treated with methanesulfonyl chloride or p-toluenesulfonyl chloride in an inert solvent (e.g., tetrahydrofuran, dioxane, dichloromethane, dichloroethane or chloroform, preferably dichloromethane) at a temperature ranging from room temperature to the boiling point of the reaction mixture, preferably at room temperature, to convert $(CH_2)_m OH$ in compound (VI*) into $(CH_2)_m—O—SO_2CH_3$ or $(CH_2)_m—SO_2—C_6H_4$-p-$CH_3$. The compound thus obtained is then treated with a metal halide (e.g., sodium iodide or potassium iodide) in an inert solvent (e.g., acetone, tetrahydrofuran, dioxane, dichloromethane, dichloroethane or chloroform, preferably acetone) at a temperature ranging from room temperature to the boiling point of the reaction mixture, preferably at the boiling point of the reaction mixture, to give compound (VII*).

In the presence of a base (e.g., sodium hydride, sodium hydroxide or potassium t-butoxide), compound (VII*) is reacted with a malonic ester of formula (VIII) (e.g., diethyl malonate or dimethyl malonate) in an inert solvent (e.g., tetrahydrofuran, dioxane, dimethylformamide, dichloromethane, dichloroethane or chloroform, preferably tetrahydrofuran) at a temperature ranging from room temperature to the boiling point of the reaction mixture to give compound (IX*).

In the presence of a base (e.g., sodium hydride, sodium hydroxide or potassium t-butoxide), compound (IX*) is reacted with an alkylating agent of formula (X) in an inert solvent (e.g., tetrahydrofuran, diethyl ether, dioxane, dimethylformamide, dichloromethane, dichloroethane or chloroform, preferably tetrahydrofuran) at a temperature ranging from room temperature to the boiling point of the reaction mixture to give compound (XI*).

Compound (XI*) is treated with sodium hydroxide or potassium hydroxide in a solvent (e.g., water, ethanol, methanol, a water/ethanol mixture or a water/methanol mixture) at a temperature ranging from room temperature to the boiling point of the reaction mixture, preferably at the boiling point of the reaction mixture, to give compound (XII*).

In a solvent (e.g., dimethyl sulfoxide, dimethylformamide, benzene, toluene, xylene, dioxane or tetrahydrofuran) and, if necessary, in the presence of an acid (e.g., hydrogen chloride, sulfuric acid or p-toluenesulfonic acid), compound (XII*) is heated to a temperature ranging from 50° C. to the boiling point of the reaction mixture to give compound (XIII*).

Next, compound (XIII*) is subjected to deprotection of the phenolic hydroxyl group to give compound (XIV*).
[Process 2]

Compound (XIV*) may also be synthesized from compound (XII*) in the following manner. A procedure analogous to Process 1 is repeated until compound (XII*) is prepared.

Compound (XII*) is subjected to deprotection of the phenolic hydroxyl group to give compound (XV*).

In a solvent (e.g., dimethyl sulfoxide, dimethylformamide, benzene, toluene, xylene, dioxane or tetrahydrofuran) and, if necessary, in the presence of an acid (e.g., hydrogen chloride, sulfuric acid or p-toluenesulfonic acid), compound (XV*) is heated to a temperature ranging from 50° C. to the boiling point of the reaction mixture to give compound (XIV*).
[Process 3]

Compound (XIV*) can also be prepared from compound (VII*) in the following manner.

In the presence of a base (e.g., sodium hydride, sodium hydroxide or potassium t-butoxide), compound (VII*) is reacted with compound (XVI) in an inert solvent (e.g., tetrahydrofuran, dioxane, dimethylformamide, dichloromethane, dichloroethane or chloroform, preferably tetrahydrofuran) at a temperature ranging from −78° C. to the boiling point of the reaction mixture to give compound (XI*).

Compound (XI*) is converted into compound (XIV*) as in Process 1 or 2.
[Process 4]

Compound (XIV*) may also be prepared in the following manner.

In the presence of a catalyst such as benzylidene-bis (tricyclohexylphosphine)dichlororuthenium, compound (XVII*) is reacted with compound (XVIII) in a solvent (e.g., methylene chloride, chloroform, benzene, toluene, xylene, dioxane, tetrahydrofuran, dimethyl sulfoxide or dimethylformamide) at a temperature ranging from −78° C. to the boiling point of the reaction mixture, preferably at the boiling point of the reaction mixture, to give compound (XIX*).

Using a catalyst (e.g., palladium on activated carbon, palladium hydroxide, platinum oxide or Wilkinson's catalyst), compound (XIX*) is hydrogenated in an inert solvent (e.g., methanol, ethanol, ethyl acetate, tetrahydrofuran, dioxane, dichloromethane, dichloroethane, chloroform or benzene) at a temperature ranging from room temperature to the boiling point of the reaction mixture, preferably at room temperature, to give compound (XX*).

Compound (XX*) is converted into compound (XIV*) as in Process 1 or 2 where compound (XI*) is converted into compound (XIV*).

[Process 5]

Further, compound (XIV*) may also be prepared in the following manner.

In the presence of a catalyst such as benzylidene-bis (tricyclohexylphosphine)dichlororuthenium, compound (XVII*) is reacted with compound (XXI) in a solvent (e.g., methylene chloride, chloroform, benzene, toluene, xylene, dioxane, tetrahydrofuran, dimethyl sulfoxide or dimethylformamide) at a temperature ranging from −78° C. to the boiling point of the reaction mixture, preferably at the boiling point of the reaction mixture, to give compound (XXII*).

Using a catalyst (e.g., palladium on activated carbon, palladium hydroxide, platinum oxide or Wilkinson's catalyst), compound (XXII*) is hydrogenated in an inert solvent (e.g., methanol, ethanol, ethyl acetate, tetrahydrofuran, dioxane, dichloromethane, dichloroethane or benzene) at a temperature ranging from room temperature to the boiling point of the reaction mixture, preferably at room temperature, to give compound (XXIII*).

Compound (XXIII*), which is identical with compound (XI*) in Process 1, is converted into compound (XIV*) as in Process 1 or 2 where compound (XI*) is converted into compound (XIV*).

Compound (XVII*) used in Processes 4 and 5 can be prepared by either Process 6 or 7 shown below.

Reaction Scheme 6 (Process 6)

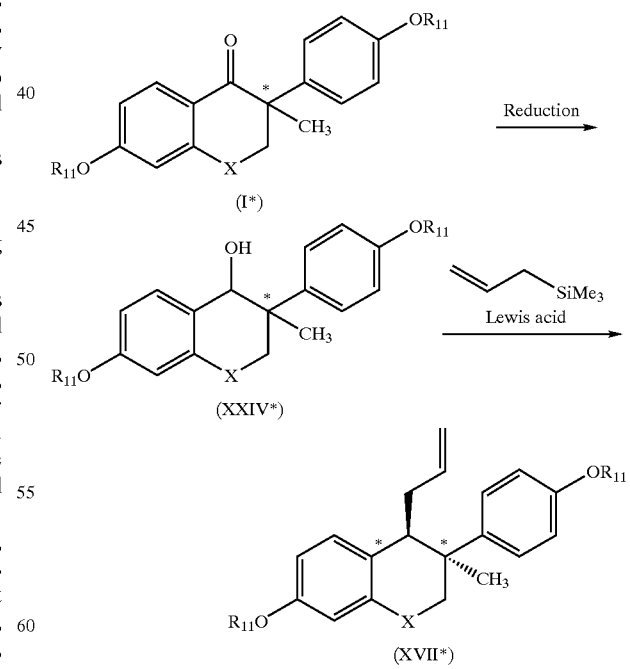

In the above Reaction Scheme 6 (Process 6), X is as defined above in general formulae (1) to (4); and $R_{11}$ represents a protecting group.

Reaction Scheme 7 (Process 7)

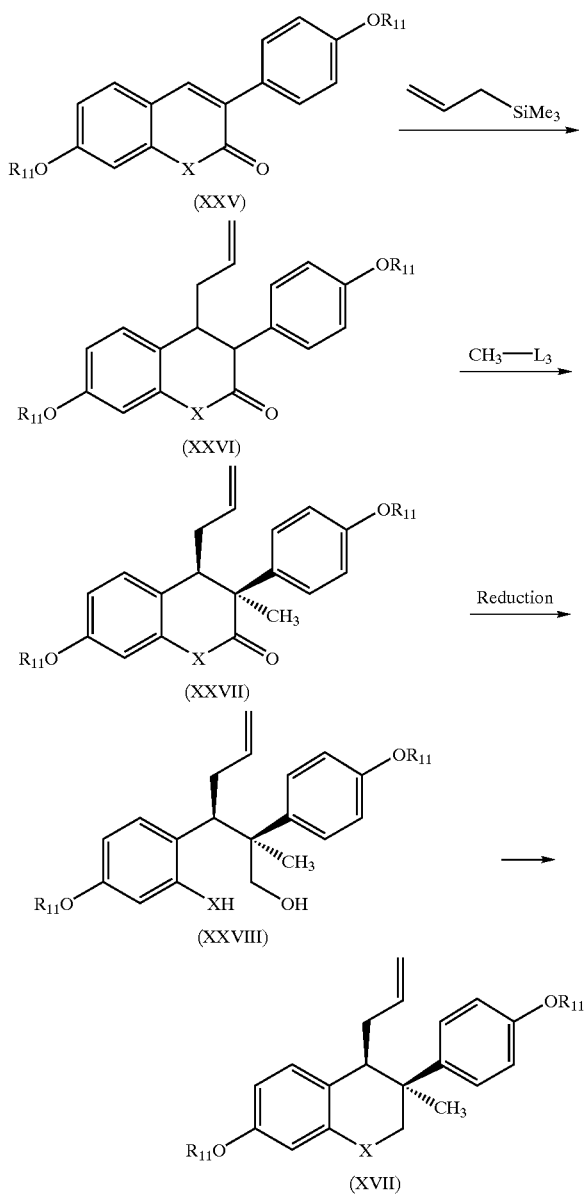

In the above Reaction Scheme 7 (Process 7), X is as defined above in general formulae (1) to (4); $R_{11}$ represents a protecting group; and $L_3$ represents a leaving group.

[Process 6] Preparation of Compound (XVII*)-Part I

Compound (I*) is reduced with lithium aluminum hydride or diisobutylaluminum hydride in an inert solvent (e.g., diethyl ether, benzene, toluene, xylene, dioxane or tetrahydrofuran) at a temperature ranging from −78° C. to the boiling point of the reaction mixture to give compound (XXIV*).

In the presence of a Lewis acid such as zinc iodide, compound (XXIV*) is reacted with allyltrimethylsilane in an inert solvent (e.g., tetrahydrofuran, dioxane, dichloromethane, dichloroethane or chloroform, preferably dichloroethane) at a temperature ranging from −78° C. to the boiling point of the reaction mixture, preferably from 0° C. to room temperature, to give compound (XVII*).

[Process 7] Preparation of Compound (XVII)-Part II

In the presence of anhydrous TBAF and, if necessary, accompanied by addition of HMPA, compound (XXV) is reacted with allyltrimethylsilane in an inert solvent (e.g., dimethylformamide, dimethyl sulfoxide, tetrahydrofuran, dioxane, dichloromethane, dichloroethane or chloroform) at a temperature ranging from −78° C. to the boiling point of the reaction mixture, preferably from 0° C. to room temperature, to give compound (XXVI).

In the presence of a base (e.g., lithium hexamethyldisilazide, n-butyllithium, s-butyllithium, sodium hydride), compound (XXVI) is reacted with an alkylating agent ($CH_3$—$L_3$) in an inert solvent (e.g., tetrahydrofuran, ether, dioxane, dichloromethane, chloroform, preferably tetrahydrofuran or dioxane) at a temperature ranging from −78° C. to the boiling point of the reaction mixture, preferably from −78° C. to room temperature, to give compound (XXVII).

Compound (XXVII) is reduced with lithium aluminum hydride in an inert solvent (e.g., tetrahydrofuran, dioxane or diethyl ether) at a temperature ranging from −78° C. to the boiling point of the reaction mixture to give compound (XXVIII).

Compound (XXVIII) is reacted with diethyl azodicarboxylate and triphenylphosphine in an inert solvent (e.g., toluene, dioxane, dimethylformamide, dimethyl sulfoxide, tetrahydrofuran, dichloromethane, dichloroethane or chloroform) at a temperature ranging from −78° C. to the boiling point of the reaction mixture, preferably from 0° C. to room temperature, to give compound (XVII).

Compound (XIV*) given by the above Processes 1 to 5 may also be converted into a salt form because it has a carboxyl group. Pharmaceutically acceptable salts include, but are not limited to, sodium, potassium, calcium and magnesium salts. For example, a salt of compound (XIV*) can be prepared as follows.

Sodium methoxide is added to compound (XIV*) dissolved in an organic solvent (e.g., dry methanol) at an appropriate temperature, for example, at room temperature, and the resulting mixture is stirred for about 30 minutes to about 3 hours at the same temperature. After addition of an organic solvent such as dry diethyl ether, the reaction mixture is evaporated under reduced pressure to remove the solvent, thereby obtaining a salt of the compound.

The compound of the present invention exists as various enantiomers because it contains three asymmetric carbon atoms. To obtain a single stereoisomer, there are two techniques, one of which uses a chiral column to resolve a mixture of stereoisomers and the other involves asymmetric synthesis. The chiral column technique may be carried out using a column commercially available from DAICEL under the trade name of CHIRALPAK-OT(+), OP(+) or AD, or CHIRALCEL-OA, OB, OJ, OK, OC, OD, OF or OG, for example. Regarding asymmetric synthesis, the following will illustrate the asymmetric synthesis of the inventive compound with respect to an asymmetric carbon atom, to which a side chain carboxyl group is attached.

Reaction Scheme 8 (Process 8)

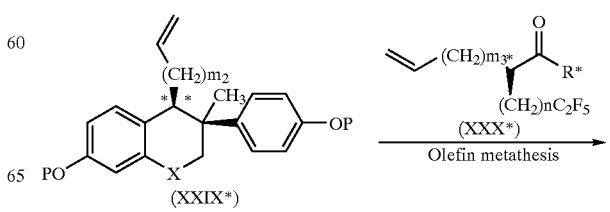

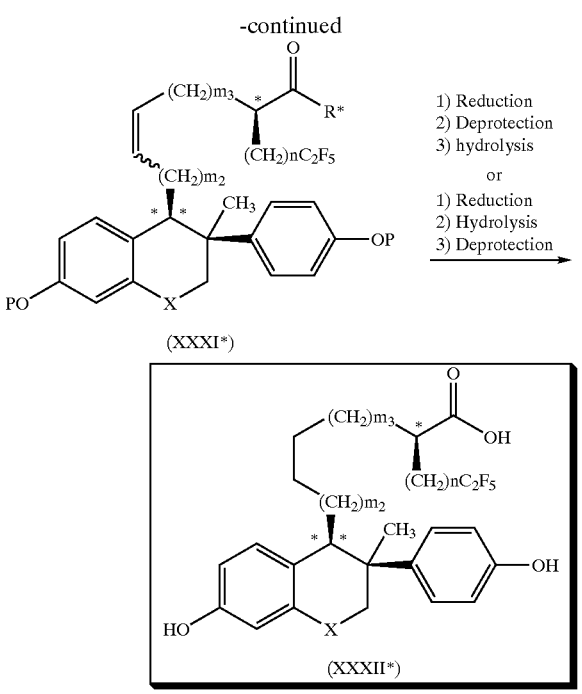

(XXXI*)

(XXXII*)

Reaction Scheme 9 (Process 9)

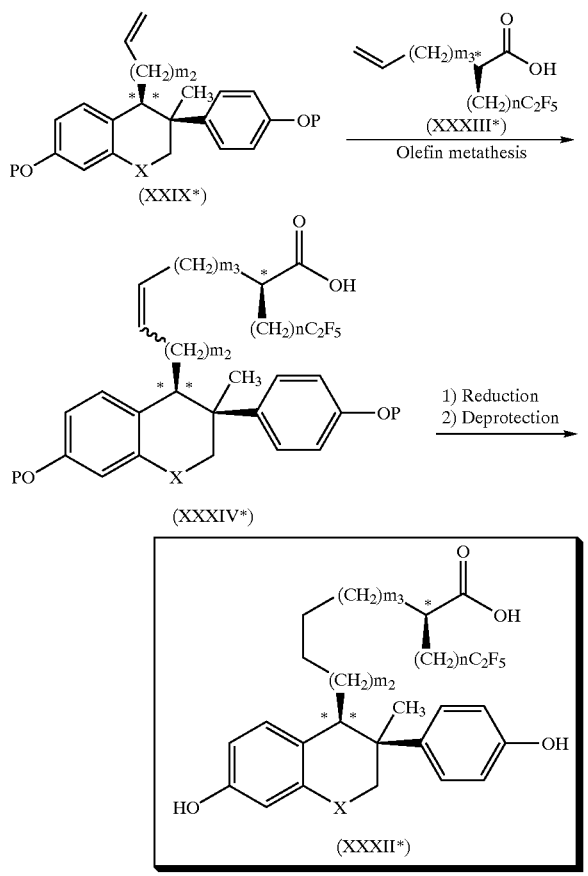

(XXIX*)

(XXXIV*)

(XXXII*)

[Process 8]

In the presence of a catalyst such as benzylidene-bis(tricyclohexylphosphine)dichlororuthenium, compound (XXIX*) is reacted with compound (XXX*) in a solvent (e.g., methylene chloride, chloroform, benzene, toluene, xylene, dioxane, tetrahydrofuran, dimethyl sulfoxide or dimethylformamide) at a temperature ranging from −78° C. to the boiling point of the reaction mixture, preferably at the boiling point of the reaction mixture, to give compound (XXXI*).

Compound (XXXI*) is then subjected to the following reactions in the order stated, (a) reduction, deprotection and hydrolysis or (b) reduction, hydrolysis and deprotection, to give compound (XXXII*).

(a) Reduction, Deprotection and Hydrolysis
1) Reduction

In the presence of a catalyst (e.g., palladium on activated carbon, palladium hydroxide, platinum oxide or Wilkinson's catalyst), compound (XXXI*) is hydrogenated in an inert solvent (e.g., methanol, ethanol, ethyl acetate, tetrahydrofuran, dioxane or benzene) at a temperature ranging from 0° C. to the boiling point of the reaction mixture, preferably at room temperature, to give a reduction product.

2) Deprotection

Next, deprotection of the phenolic hydroxyl group is carried out to give a deprotected product.

3) Hydrolysis

By way of example, if R* is a group of formula (XXXVIII*), the deprotected product is further treated with lithium hydroxide, sodium hydroxide, lithium hydroxide plus hydrogen peroxide, sodium hydroxide plus hydrogen peroxide, or tetrabutylammonium hydroxide plus hydrogen peroxide in a solvent (e.g., a tetrahydrofuran/water mixture, a diethyl ether/water mixture, a dioxane/water mixture, a methanol/water mixture, an ethanol/water mixture) at a temperature ranging from room temperature to the boiling point of the reaction mixture, preferably at room temperature, to give compound (XXXII*).

(b) Reduction, Hydrolysis and Deprotection
1) Reduction

In the presence of a catalyst (e.g., palladium on activated carbon, palladium hydroxide, platinum oxide or Wilkinson's catalyst), compound (XXXI*) is hydrogenated in an inert solvent (e.g., methanol, ethanol, ethyl acetate, tetrahydrofuran, dioxane or benzene) at a temperature ranging from 0° C. to the boiling point of the reaction mixture, preferably at room temperature, to give a reduction product.

2) Hydrolysis

By way of example, if R* is a group of formula (XXXVIII*), the reduction product is further treated with lithium hydroxide, sodium hydroxide, lithium hydroxide plus hydrogen peroxide, sodium hydroxide plus hydrogen peroxide, or tetrabutylammonium hydroxide plus hydrogen peroxide in a solvent (e.g., a tetrahydrofuran/water mixture, a diethyl ether/water mixture, a dioxane/water mixture, a methanol/water mixture, an ethanol/water mixture) at a temperature ranging from room temperature to the boiling point of the reaction mixture, preferably at room temperature, to give a carboxylic acid.

3) Deprotection

Next, deprotection of the phenolic hydroxyl group is carried out to give compound (XXXII*).

[Process 9]

In the presence of a catalyst such as benzylidene-bis(tricyclohexylphosphine)dichlororuthenium, compound (XXIX*) is reacted with compound (XXXIII*) in a solvent (e.g., methylene chloride, chloroform, benzene, toluene, xylene, dioxane, tetrahydrofuran, dimethyl sulfoxide or dimethylformamide) at a temperature ranging from −78° C. to the boiling point of the reaction mixture, preferably at the boiling point of the reaction mixture, to give compound (XXXIV*).

In the presence of a catalyst (e.g., palladium on activated carbon, palladium hydroxide, platinum oxide or Wilkinson's catalyst), compound (XXXIV*) is hydrogenated in an inert solvent (e.g., methanol, ethanol, ethyl acetate, tetrahydrofuran, dioxane or benzene) at a temperature ranging from 0° C. to the boiling point of the reaction mixture, preferably at room temperature, to give a reduction product.

Next, deprotection of the phenolic hydroxyl group is carried out to give compound (XXXII*).

The chiral olefins of formulae (XXX*) and (XXXIII*) used in the above Processes 8 and 9, respectively, may be synthesized as follows (Reaction Scheme 10).

preferably tetrahydrofuran) at a temperature ranging from −78° C. to the boiling point of the reaction mixture, preferably from −30° C. to room temperature, to give compound (XXX*).

In the presence of a nucleophilic reagent (e.g., lithium hydroxide plus hydrogen peroxide, lithium hydroxide, sodium methoxide, sodium thioethoxide) or an acid (e.g., hydrochloric acid, sulfuric acid), compound (XXX*) is hydrolyzed in an inert solvent (e.g., methanol, ethanol, Reaction Scheme 10

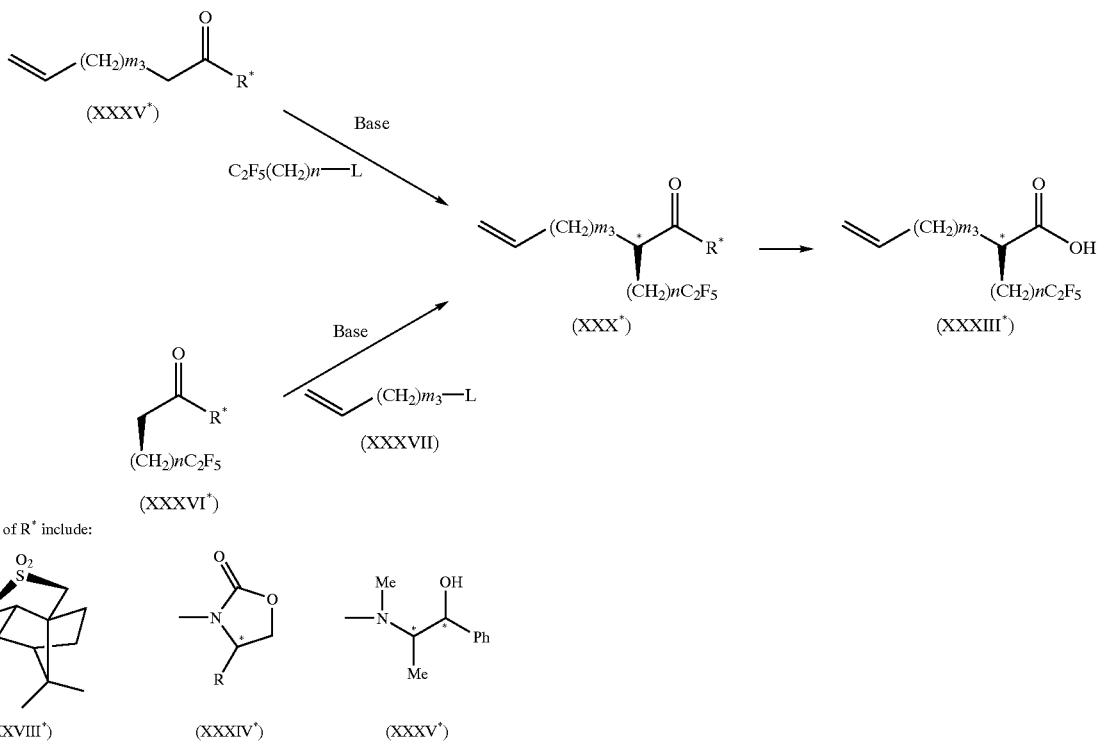

In the above Reaction Schemes 8, 9 and 10 (Processes 8, 9 and 10), X, m and n are as defined above in general formula (1); R* represents a chiral auxiliary group; P represents a leaving group; L represents a leaving group; and $m_2$ and $m_3$ are integers that satisfy the relation $m=m_2+m_3+2$. The symbol R in formula (XXXIV*) represents an alkyl group.

Synthesis of Chiral Olefins

In the presence of a base (e.g., lithium diisopropylamide, lithium hexamethyl-disilazide, sodium hexamethyl-disilazide, butyllithium) and HMPA, compound (XXXV*) is reacted with $C_2F_5(CH_2)_n$—L in an inert solvent (e.g., tetrahydrofuran, toluene, diethyl ether, hexane, preferably tetrahydrofuran) at a temperature ranging from −78° C. to the boiling point of the reaction mixture, preferably from −30° C. to room temperature, to give compound (XXX*).

Alternatively, in the presence of a base (e.g., lithium diisopropylamide, lithium hexamethyl-disilazide, sodium hexamethyl-disilazide, butyllithium) and HMPA, compound (XXXVI*) is reacted with compound (XXXVII) in an inert solvent (e.g., tetrahydrofuran, toluene, diethyl ether, hexane, tetrahydrofuran, water, preferably a tetrahydrofuran/water mixture) at a temperature ranging from −78° C. to the boiling point of the reaction mixture, preferably from room temperature to 50° C., to convert the chiral auxiliary group thereby giving compound (XXXIII*).

EXAMPLES

The present invention is more specifically explained by the following examples. However, it should be understood that the present invention is not limited to these examples in any manner. In order to explain the effectiveness of the compounds according to the present invention, typical compounds were tested for their anti-estrogenic activity in the test example shown below. Table 1 shows chemical structures of the compounds prepared in the examples.

TABLE 1

General formula (1)

General formula (2)

| Example No. | Formula | X | m | n |
|---|---|---|---|---|
| 2 | (2) | S | 8 | 3 |
| 3 | (1) | S | 8 | 3 |
| 4 | (2) | S | 9 | 3 |
| 5 | (1) | S | 9 | 3 |
| 7 | (1) or (2) | O | 9 | 3 |
| 8 | (1) or (2) | O | 9 | 3 |
| 10, Peak 1 | (2) | S | 8 | 3 |
| 10, Peak 2 | (2) | S | 8 | 3 |
| 11, Peak 1 | (1) | S | 8 | 3 |
| 11, Peak 2 | (1) | S | 8 | 3 |

Example 1

Optical Resolution of 7-Methoxy-3-(4-methoxyphenyl)-3-methylthiochroman-4-one

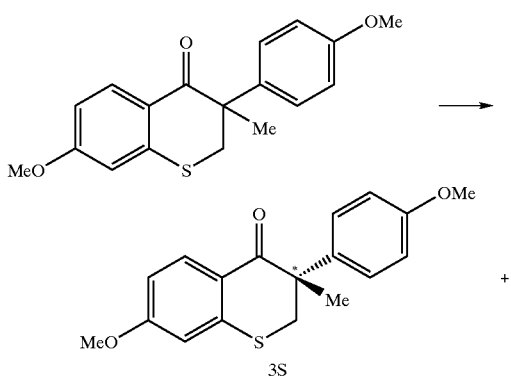

Optical resolution of 7-methoxy-3-(4-methoxyphenyl)-3-methylthiochroman-4-one was carried out using a chiral column (CHIRALCEL OD) to give (3R)-7-methoxy-3-(4-methoxyphenyl)-3-methylthiochroman-4-one and (3S)-7-methoxy-3-(4-methoxyphenyl)-3-methylthiochroman-4-one.

Example 2

Synthesis of 10-[(3R,4R)-7-Hydroxy-3-(4-hydroxyphenyl)-3-methylthiochroman-4-yl]-2-(4,4,5,5,5-pentafluoropentyl)decanoic Acid (Step 1)

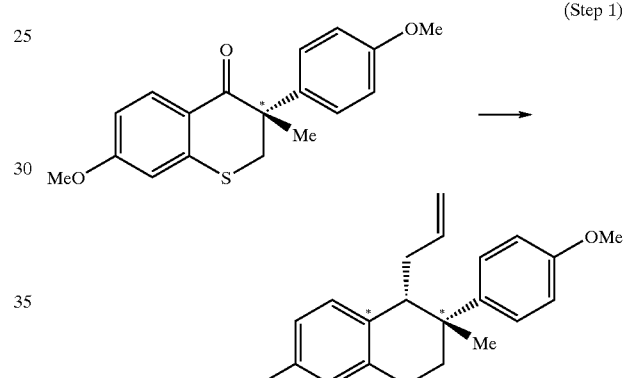

A solution of the (3S)-7-methoxy-3-(4-methoxyphenyl)-3-methylthiochroman-4-one prepared in Example 1 (15 g, 0.048 mol) in anhydrous tetrahydrofuran (250 ml) was cooled to −78° C. To this solution, lithium aluminum hydride (905 mg, 0.024 mol) was added dropwise and the resulting mixture was stirred for 12 hours at room temperature. After the reaction was completed, saturated aqueous ammonium chloride was added to the reaction mixture, which was then extracted three times with ethyl acetate. The combined organic layers were washed with water and saturated aqueous sodium chloride, and then dried over anhydrous magnesium sulfate. After distilling off the solvent, zinc iodide (18.0 g, 0.053 mol) and allyltrimethylsilane (15 ml, 0.088 mol) were added dropwise to a solution of the residue in 1,2-dichloroethane (300 ml) while cooling at 0° C., followed by stirring overnight at room temperature. After the reaction was completed, water was added to the reaction mixture, which was then extracted three times with dichloromethane. The combined organic layers were washed with water and saturated aqueous sodium chloride, and then dried over anhydrous magnesium sulfate. After distilling off the solvent, the residue was purified by silica gel column chromatography (eluent: ethyl acetate/hexane=1/4) to give (3R,4R)-7-methoxy-3-(4-methoxyphenyl)-3-methyl-4-(2-propenyl)thiochroman (10.8 g, Yield 67%).

$^1$H-NMR (270 MHz, CDCl$_3$): δ 7.27 (d, 2H, J=7.2 Hz), 6.91–6.87 (m, 3H), 6.71 (s, 1H), 6.55 (dd, 1H, J=8.9, 2.4

Hz), 5.65–5.48 (m, 1H), 4.85 (d, 1H, J=9.8 Hz), 4.66 (d, 1H, J=17.0 Hz), 3.81 (s, 3H), 3.76 (s, 3H), 3.60 (d, 1H, J=12.1 Hz), 2.98 (d, 1H, J=12.1 Hz), 2.91–2.88 (m, 1H), 1.96–1.82 (m, 2H), 1.21 (t, 3H, J=7.2 Hz).

(Step 2)

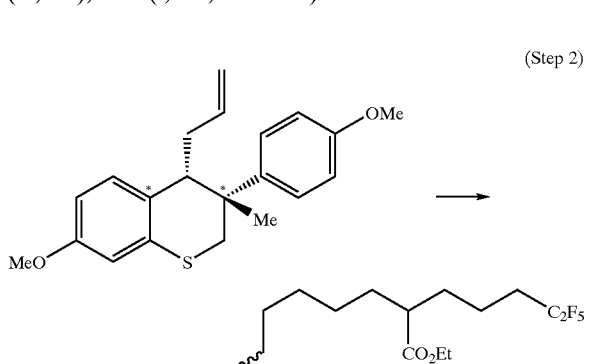

Ethyl 2-(4,4,5,5,5-pentafluoropentyl)-8-nonenoate was separately prepared from 1-iodo-4,4,5,5,5-pentafluoropentane, diethyl malonate and 1-iodo-6-heptene. A solution of this compound (4.55 g, 13.21 mmol), (3R,4R)-7-methoxy-3-(4-methoxyphenyl)-3-methyl-4-(2-propenyl)thiochroman (2.5 g, 7.342 mmol) and benzylidene-bis(tricyclohexylphosphine)dichlororuthenium (302 mg, 0.367 mmol) in dichloromethane (60 ml) was heated under reflux for 6 hours. After the reaction was completed, the solvent was distilled off and the resulting residue was purified by silica gel column chromatography (eluent: ethyl acetate/hexane=1/30) to give ethyl 10-[(3R,4R)-7-methoxy-3-(4-methoxyphenyl)-3-methylthiochroman-4-yl]-2-(4,4,5,5,5-pentafluoropentyl)-8-decenoate (3.46 g, Yield 72%) as an oil.

$^1$H-NMR (270 MHz, CDCl$_3$): δ 7.34 (d, 2H), 6.95 (m, 3H), 6.75 (d, 1H), 6.58 (m, 1H), 5.42~4.61 (m, 2H), 4.20 (m, 3H), 3.82 (d, 6H), 3.65 (d, 1H), 2.98 (m, 1H), 2.75 (bs, 1H), 2.32 (m, 2H), 2.12~0.98 (m, 22H).

(Step 3)

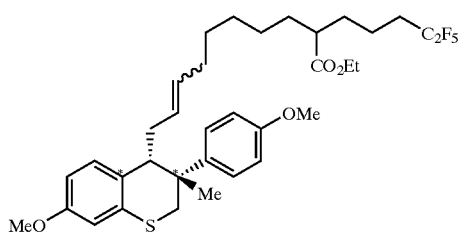

-continued

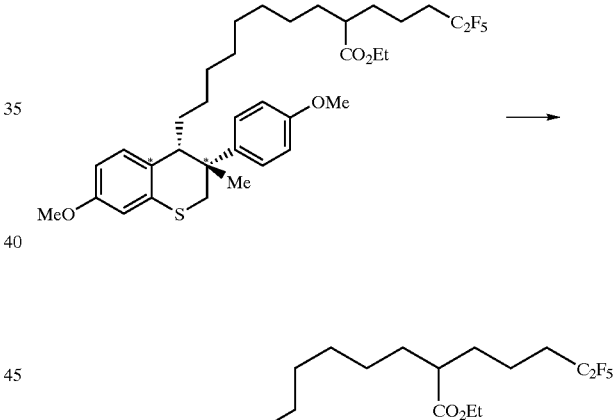

10% Pd/C (1.04 g) was added to a solution of the ethyl 10-[(3R,4R)-7-methoxy-3-(4-methoxyphenyl)-3-methylthiochroman-4-yl]-2-(4,4,5,5,5-pentafluoropentyl)-8-decenoate (3.46 g, 5.268 mmol) in tetrahydrofuran (60 ml) followed by stirring for 23 hours at room temperature under a hydrogen stream. After the reaction mixture was filtered, the solvent was distilled off and the resulting residue was purified by silica gel column chromatography (eluent: ethyl acetate/hexane=1/10) to give ethyl 10-[(3R,4R)-7-methoxy-3-(4-methoxyphenyl)-3-methylthiochroman-4-yl]-2-(4,4,5,5,5-pentafluoropentyl)decanoate (3.23 g, Yield 93%) as an oil.

$^1$H-NMR (270 MHz, CDCl$_3$): δ 7.28 (d, 2H), 6.88 (m, 3H), 6.70 (m, 1H), 6.61~6.55 (dd, 1H), 4.10 (q, 2H), 3.77 (d, 6H), 3.62 (d, 1H), 2.98 (d, 1H), 2.75 (bs, 1H), 2.31 (m, 1H), 2.11~1.89 (m, 2H), 1.73~0.98 (m, 26H).

(Step 4)

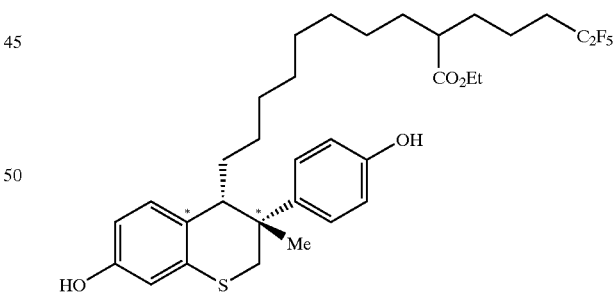

A solution of ethyl 10-[(3R,4R)-7-methoxy-3-(4-methoxyphenyl)-3-methylthiochroman-4-yl]-2-(4,4,5,5,5-pentafluoropentyl)decanoate (3.23 g, 4.902 mmol) in dichloromethane (60 ml) was cooled to −78° C. To this solution, a solution of boron tribromide in dichloromethane (1M, 39.22 ml, 39.22 mmol) was slowly added dropwise, and the resulting mixture was stirred for 1 hour. The reaction vessel was then transferred to an ice-bath and the reaction mixture was further stirred for 3 hours. After the reaction was completed, water was added to the reaction mixture, which was then extracted with dichloromethane. The organic layer was dried over anhydrous magnesium sulfate. After distilling off the solvent, the residue was purified by silica gel column chromatography (eluent: ethyl acetate/n-hexane=1/20) to give ethyl 10-[(3R,4R)-7-hydroxy-3-(4-hydroxyphenyl)-3-methylthiochroman-4-yl]-2-(4,4,5,5,5-pentafluoropentyl)decanoate (2.08 g, Yield 67%) as a foam.

$^1$H-NMR (270 MHz, CDCl$_3$): δ 7.22 (d, 2H), 6.80 (m, 3H), 6.68 (m, 1H), 6.43 (d, 1H), 5.81 (d, 1H), 5.01 (d, 1H), 4.10 (q, 2H), 3.61 (d, 1H), 2.96 (d, 1H), 2.68 (bs, 1H), 2.38 (m, 1H), 2.17~1.91 (m, 2H), 1.67~0.98 (m, 26H).

(Step 5)

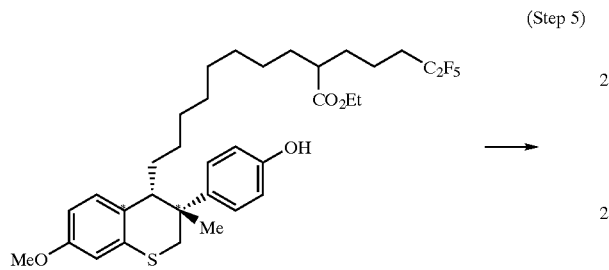

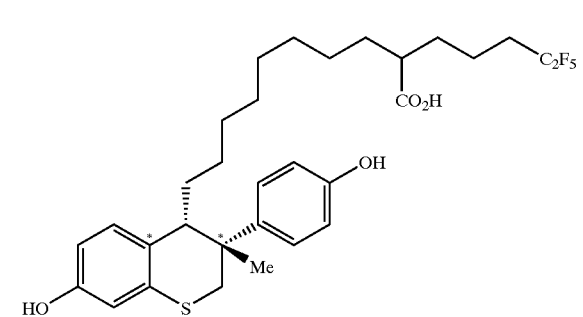

Ethyl 10-[(3R,4R)-7-hydroxy-3-(4-hydroxyphenyl)-3-methylthiochroman-4-yl]-2-(4,4,5,5,5-pentafluoropentyl)decanoate (2.08 g, 3.297 mmol) and sodium hydroxide (527 mg, 13.19 mmol) were added to an ethanol/water mixture (40/10 ml), followed by heating under reflux for 4 hours. The reaction mixture was acidified with 2N hydrochloric acid and then extracted with ethyl acetate. The organic layer was dried over anhydrous magnesium sulfate. After distilling off the solvent, the residue was purified by silica gel column chromatography (eluent: ethyl acetate/hexane/dichloromethane=1/4/1) to give 10-[(3R,4R)-7-hydroxy-3-(4-hydroxyphenyl)-3-methythiochroman-4-yl]-2-(4,4,5,5,5-pentafluoropentyl)decanoic acid (1.8 g, Yield 91%) as a foam.

$^1$H-NMR (270 MHz, CDCl$_3$): δ 7.22 (d, 2H), 6.82 (m, 3H), 6.64 (d, 1H), 6.52 (dd, 1H), 3.59 (d, 1H), 2.95 (d, 1H), 2.65 (bs, 1H), 2.37 (m, 1H), 2.12~1.91 (m, 2H), 1.74~1.42 (m, 6H), 1.32~0.98 (m, 17H).

Example 3

Synthesis of 10-[(3S,4S)-7-Hydroxy-3-(4-hydroxyphenyl)-3-methylthiochroman-4-yl]-2-(4,4,5,5,5-pentafluoropentyl)decanoic Acid (Step 1)

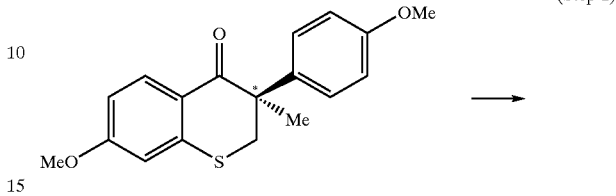

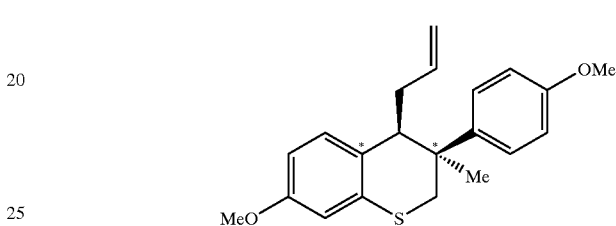

The (3R)-7-methoxy-3-(4-methoxyphenyl)-3-methylthiochroman-4-one prepared in Example 1 (11.4 g, 36.26 mmol) was dissolved in tetrahydrofuran (40 ml) and ethanol (20 ml). To this solution, sodium borohydride (2.74 g, 72.51 mmol) was added at −78° C., and the resulting mixture was stirred for 15 hours at room temperature. After the reaction was completed, dichloromethane, methanol and saturated aqueous sodium chloride were added to the reaction mixture, which was then extracted under heating conditions. The organic layer was dried over anhydrous magnesium sulfate. After distilling off the solvent, allyltrimethylsilane (10.74 ml, 67.6 mmol) and zinc iodide (12.9 g, 40.57 mmol) were added to a solution of the residue in dichloromethane (300 ml) followed by stirring for 15 hours at room temperature. Water was added to the reaction mixture, which was then extracted with dichloromethane. The organic layer was washed with saturated aqueous ammonium chloride and dried over anhydrous magnesium sulfate, and the resulting residue was purified by silica gel column chromatography (eluent: ethyl acetate/hexane=1/90) to give (3S,4S)-7-methoxy-3-(4-methoxyphenyl)-3-methyl-4-(2-propenyl)thiochroman (7.2 g, Yield 58%) as an oil.

$^1$H-NMR (270 MHz, CDCl$_3$): δ 7.32 (d, 2H), 6.91 (m, 3H), 6.75 (d, 1H), 6.57 (dd, 1H), 5.45 (m, 1H), 4.83 (d, 1H), 4.67 (d, 1H), 3.81 (d, 6H), 3.65 (d, 1H), 3.02 (d, 1H), 2.87 (d, 1H), 1.9 (m, 2H), 1.31 (s, 3H).

(Step 2)

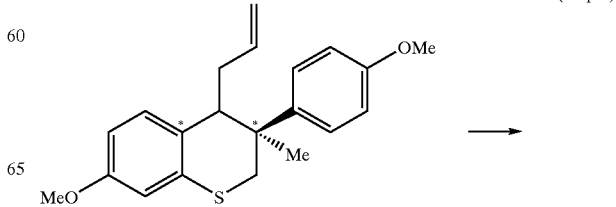

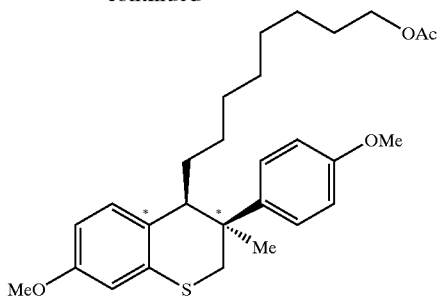

Benzylidene-bis(tricyclohexylphosphine)-dichlororuthenium (1.2 g, 1.5 mmol) was added to a solution of (3S,4S)-7-methoxy-3-(4-methoxyphenyl)-3-methyl-4-(2-propenyl)thiochroman (7.1 g, 20.85 mmol) and 1-acetoxy-6-heptene (7.32 ml, 41.7 mmol) in dichloromethane (100 ml), followed by heating under reflux for 8 hours. The reaction mixture was concentrated under reduced pressure and the resulting residue was purified by silica gel column chromatography (eluent: ethyl acetate/hexane=1/20) to give the desired olefin. Pd/C (2.2 g) was added to a solution of this olefin in ethyl acetate (80 ml) followed by stirring for 20 hours under a hydrogen stream. The reaction mixture was filtered and concentrated under reduced pressure to give 1-acetoxy-8-[(3S,4S)-7-methoxy-3-(4-methoxyphenyl)-3-methylthiochroman-4-yl]octane (7.31 g, Yield 77.8%).

$^1$H-NMR (270 MHz, CDCl$_3$): δ 7.28 (d, J=13.19 Hz, 2H), 6.91 (m, 3H), 6.72 (s, 1H), 6.59 (dd, 1H), 4.00 (t, 2H), 3.80 (d, 6H), 3.64 (d, 1H), 2.99 (d, 1H), 2.73 (d, 1H), 2.03 (s, 3H), 1.51 (m, 2H), 1.4–0.85 (m, 15H).

(Step 3)

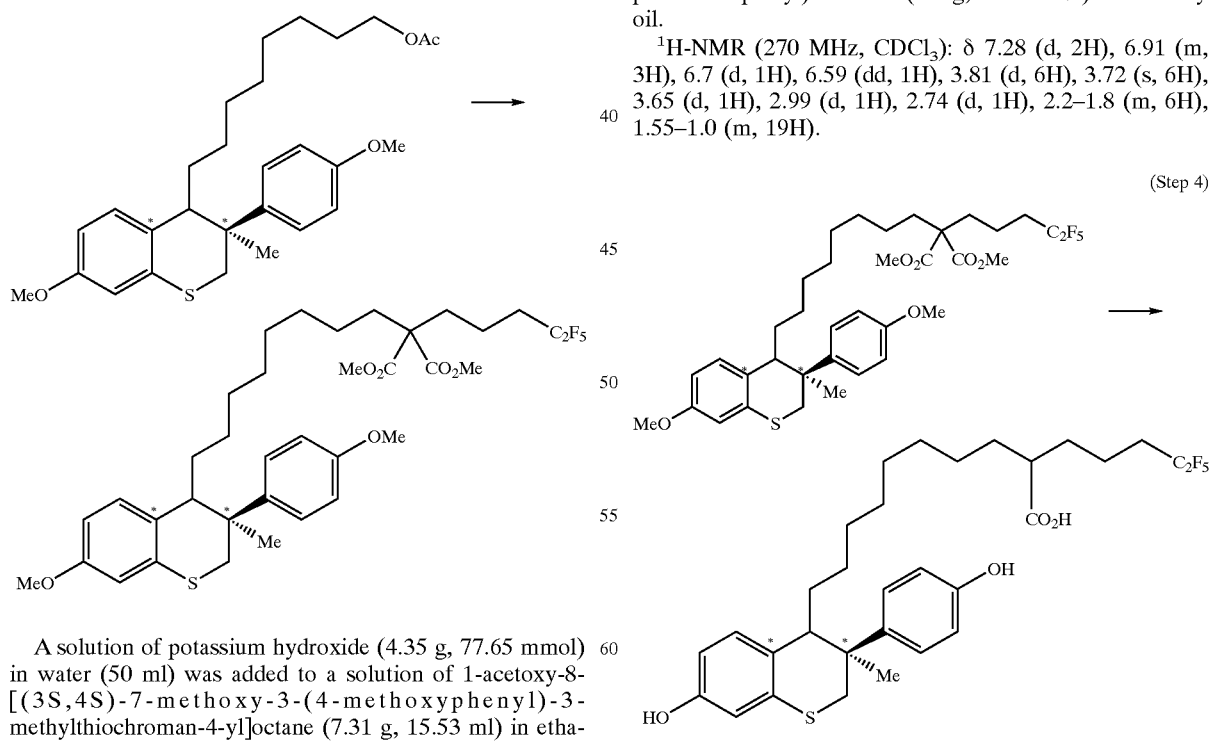

A solution of potassium hydroxide (4.35 g, 77.65 mmol) in water (50 ml) was added to a solution of 1-acetoxy-8-[(3S,4S)-7-methoxy-3-(4-methoxyphenyl)-3-methylthiochroman-4-yl]octane (7.31 g, 15.53 ml) in ethanol (100 ml), and the resulting mixture was heated with stirring under reflux for 12 hours. After the reaction mixture was concentrated under reduced pressure, water was added to the residue, which was then extracted with ethyl acetate. The organic layer was dried over anhydrous magnesium sulfate and then evaporated to remove the solvent. The residue was dissolved in dichloromethane (100 ml), and triethylamine (4.33 ml, 31.06 mmol) and methanesulfonyl chloride (1.8 ml, 23.29 mmol) were added to the solution followed by stirring for 1 hour and 30 minutes at 5° C. After the reaction was completed, water was added to the reaction mixture, which was then extracted with dichloromethane. The organic layer was dried over anhydrous magnesium sulfate and then evaporated to remove the solvent. Sodium iodide (11.6 g, 77.65 mmol) was added to a solution of the residue in acetone (200 ml), followed by heating under reflux for 3 hours. After the reaction mixture was filtered and concentrated under reduced pressure, water was added to the residue, which was then extracted with ethyl acetate. The organic layer was dried over anhydrous magnesium sulfate and then evaporated to remove the solvent. The residue was purified by silica gel column chromatography (eluent: ethyl acetate/hexane=1/10) to give 1-iodo-8-[(3S,4S)-7-methoxy-3-(4-methoxyphenyl)-3-methylthiochroman-4-yl]octane (4.0 g, 7.42 mmol). Sodium hydride (0.62 g, 15.58 mmol) was added to a solution of separately prepared dimethyl 2-(4,4,5,5,5-pentafluoropentyl)malonate (4.33 g, 14.85 mmol) in tetrahydrofuran (40 ml) followed by stirring for 30 minutes at 0° C. A solution of 1-iodo-8-[(3S,4S)-7-methoxy-3-(4-methoxyphenyl)-3-methylthiochroman-4-yl]octane in tetrahydrofuran (40 ml) was added to the resulting mixture followed by stirring for 24 hours at room temperature. Water was added to the reaction mixture, which was then extracted with ethyl acetate. After the organic layer was dried over anhydrous magnesium sulfate, the solvent was distilled off and the resulting residue was purified by silica gel column chromatography (eluent: ethyl acetate/hexane=1/30) to give dimethyl 2-{8-[(3S,4S)-7-methoxy-3-(4-methoxyphenyl)-3-methylthiochroman-4-yl]octyl}-2-(4,4,5,5,5-pentafluoropentyl)malonate (3.7 g, Yield 71%) as a foamy oil.

$^1$H-NMR (270 MHz, CDCl$_3$): δ 7.28 (d, 2H), 6.91 (m, 3H), 6.7 (d, 1H), 6.59 (dd, 1H), 3.81 (d, 6H), 3.72 (s, 6H), 3.65 (d, 1H), 2.99 (d, 1H), 2.74 (d, 1H), 2.2–1.8 (m, 6H), 1.55–1.0 (m, 19H).

(Step 4)

A solution of potassium hydroxide (22.35 g, 398.4 mmol) in water (70 ml) was added to a solution of dimethyl 2-{8-[(3S,4S)-7-methoxy-3-(4-methoxyphenyl)-3- methylthiochroman-4-yl]octyl}-2-(4,4,5,5,5-pentafluoropentyl)malonate (7.0 g, 9.96 mmol) in ethanol (140 ml), followed by heating under reflux for 15 hours. The reaction mixture was adjusted to pH 4 by addition of hydrochloric acid at 0° C. and then concentrated under reduced pressure. Water was added to the residue, which was then extracted with ethyl acetate. The organic layer was washed with water and dried over anhydrous magnesium sulfate. After distilling off the solvent, a solution of boron tribromide in dichloromethane (1N, 59.76 ml, 59.76 mmol) was added to a solution of the residue in dichloromethane (100 ml) at −78° C. The resulting mixture was stirred and warmed to 0° C. over 3 hours. Water was added to the reaction mixture, which was then extracted with dichloromethane. The organic layer was washed with saturated aqueous sodium chloride and dried over anhydrous magnesium sulfate. After distilling off the solvent, toluene (50 ml) was added to the residue, followed by heating under reflux for 72 hours. Water was added to the reaction mixture, which was then extracted with ethyl acetate. The organic layer was washed with saturated aqueous sodium chloride and dried over anhydrous magnesium sulfate. After distilling off the solvent, the residue was purified by silica gel column chromatography (eluent: hexane/ethyl acetate/dichloromethane=5/1/1) to give 10-[(3S,4S)-7-hydroxy-3-(4-hydroxyphenyl)-3-methylthiochroman-4-yl]-2-(4,4,5,5,5-pentafluoropentyl)decanoic acid (3.4 g, Yield 57.8%).

$^1$H-NMR (270 MHz, CDCl$_3$): δ 9.20 (s, 1H), 7.22 (d, J=7.92 Hz, 2H), 6.86 (d, 1H), 6.73 (d, 2H), 6.52 (s, 1H), 6.42 (d, 1H), 3.5 (d, 1H), 3.01 (d, 1H), 2.72 (d, 1H), 2.32–2.06 (m, 3H), 1.6–0.8 (m, 23H), EI-MS: 602 (M+).

Example 4

Synthesis of 11-[(3R,4R)-7-Hydroxy-3-(4-hydroxyphenyl)-3-methylthiochroman-4-yl]-2-(4,4,5,5,5-pentafluoropentyl)undecanoic Acid

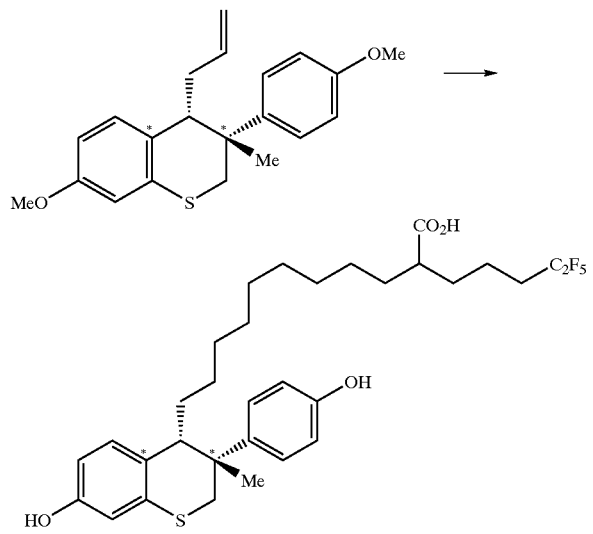

Starting with the (3R,4R)-7-methoxy-3-(4-methoxyphenyl)-3-methyl-4-(2-propenyl)thiochroman prepared in Example 2 and ethyl 2-(4,4,5,5,5-pentafluoropentyl)-9-decenoate separately prepared from 1-iodo-4,4,5,5,5-pentafluoropentane, diethyl malonate and 1-iodo-7-octene, a procedure analogous to that as shown in Example 2 or 3 was repeated to give 11-[(3R,4R)-7-hydroxy-3-(4-hydroxyphenyl)-3-methylthiochroman-4-yl]-2-(4,4,5,5,5-pentafluoropentyl)undecanoic acid.

$^1$H-NMR (270 MHz, CDCl$_3$): δ 7.22 (d, 2H), 6.82 (m, 3H), 6.64 (d, 1H), 6.52 (dd, 1H), 3.59 (d, 1H), 2.95 (d, 1H), 2.65 (bs, 1H), 2.37 (m, 1H), 2.11–1.91 (m, 2H), 1.75–1.43 (m, 6H), 1.32–0.98 (m, 19H).

Example 5

Synthesis of 11-[(3S,4S)-7-Hydroxy-3-(4-hydroxyphenyl)-3-methylthiochroman-4-yl]-2-(4,4,5,5,5-pentafluoropentyl)undecanoic Acid

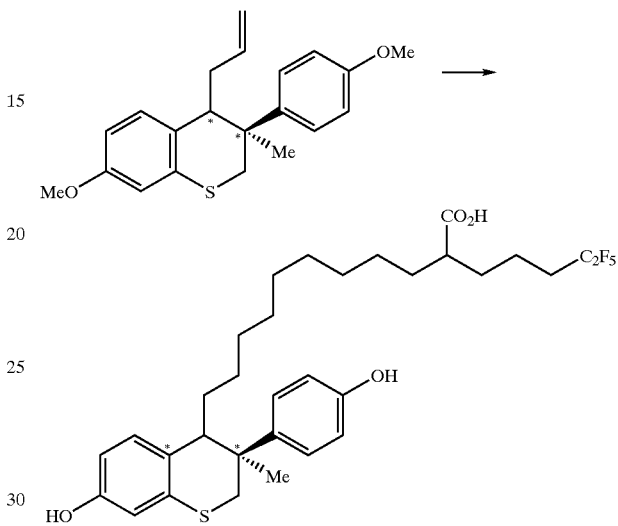

Starting with the (3S,4S)-7-methoxy-3-(4-methoxyphenyl)-3-methyl-4-(2-propenyl)thiochroman prepared in Example 3 and ethyl 2-(4,4,5,5,5-pentafluoropentyl)-9-decenoate separately prepared from 1-iodo-4,4,5,5,5-pentafluoropentane, diethyl malonate and 1-iodo-7-octene, a procedure analogous to that as shown in Example 2 or 3 was repeated to give 11-[(3S,4S)-7-hydroxy-3-(4-hydroxyphenyl)-3-methylthiochroman-4-yl]-2-(4,4,5,5,5-pentafluoropentyl)undecanoic acid.

$^1$H-NMR (270 MHz, DMSO-d6): δ 9.24 (bs, 1H), 7.23 (d, 2H, J=8.3 Hz), 6.85 (d, 1H, J=8.24 Hz), 6.73 (d, 2H, J=8.6 Hz), 6.50 (s, 1H), 6.41 (d, 1H, J=7.92 Hz), 3.52 (d, 1H), 3.02 (d, 1H), 2.74 (bs, 1H), 2.30–0.92 (m, 29H).

Example 6

Optical Resolution of 7-Hydroxy-3-(4-hydroxyphenyl)-3-methylchroman-4-one

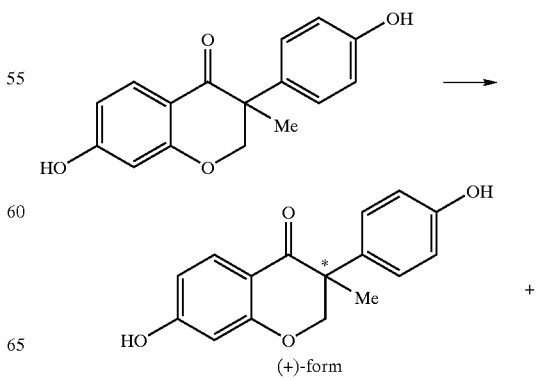

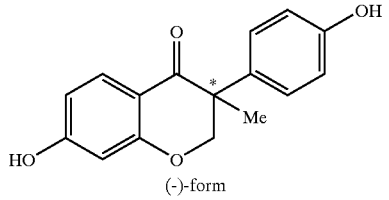

(−)-form

Optical resolution of (±)-7-hydroxy-3-(4-hydroxyphenyl)-3-methylchroman-4-one was carried out using a chiral column (CHIRALCEL OD) to give (+)-7-hydroxy-3-(4-hydroxyphenyl)-3-methylchroman-4-one and (−)-7-hydroxy-3-(4-hydroxyphenyl)-3-methylchroman-4-one.

Example 7

Synthesis of 11-[7-Hydroxy-3-(4-hydroxyphenyl)-3-methyl-chroman-4-yl]-2-(4,4,5,5,5-pentafluoropentyl)undecanoic Acid Having Chiral Carbons at Positions 3 and 4

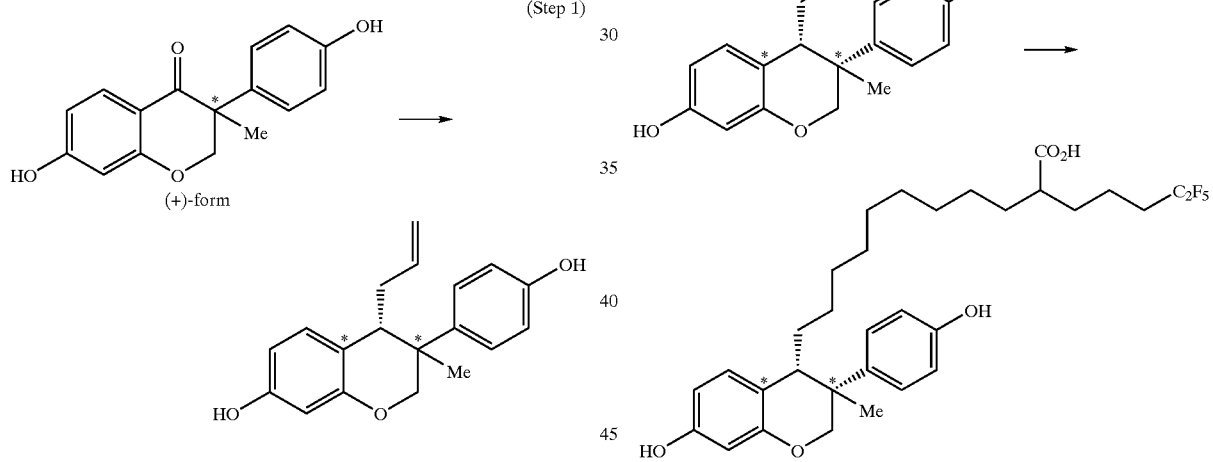

A solution of (+)-7-hydroxy-3-(4-hydroxyphenyl)-3-methylchroman-4-one (2.0 g, 7.40 mmol) in anhydrous tetrahydrofuran (30 ml) was cooled to −78° C. To this solution, a solution of diisobutylaluminum hydride in toluene (1N, 22.94 ml, 22.94 mmol) was slowly added dropwise, and the resulting mixture was stirred for 35 minutes at −78° C. Methanol (1 ml) was added to the reaction mixture at −78° C., which was then warmed to 0° C. and further saturated aqueous ammonium chloride (5 ml) and concentrated hydrochloric acid (7 ml) were added to the mixture followed by stirring for 30 minutes. The reaction mixture was extracted twice with ethyl acetate. The combined organic layers were washed with water and saturated aqueous sodium chloride, and then dried over anhydrous magnesium sulfate. After distilling off the solvent, zinc iodide (2.55 g, 7.98 mmol) was added to a suspension of the residue and allyltrimethylsilane (5.3 ml, 33.2 mmol) in 1,2-dichloroethane (80 ml) followed by stirring for 12 hours at room temperature. Saturated aqueous ammonium chloride (15 ml), methanol (10 ml) and concentrated hydrochloric acid (10 ml) were added to the reaction mixture, followed by stirring for 30 minutes. The reaction mixture was extracted twice with dichloromethane. The combined organic layers were washed with water and saturated aqueous sodium chloride, and then dried over anhydrous magnesium sulfate. After distilling off the solvent, the residue was purified by silica gel column chromatography (eluent: ethyl acetate/hexane=1/4) to give optically active 7-hydroxy-3-(4-hydroxyphenyl)-3-methyl-4-(2-propenyl)chroman (cis-configuration, 859 mg, Yield 44%).

$^1$H-NMR (270 MHz, CDCl$_3$): δ 7.10 (d, J=8.6 Hz, 2H, Ar—H), 6.91 (d, J=8.6 Hz, 1H, Ar—H), 6.84 (d, J=8.6 Hz, 2H, Ar—H), 6.3–6.4 (m, 2H, Ar—H), 6.5–6.7 (m, 1H, vinyl-H), 4.60–5.00 (br, 2H, OH), 4.86 (d, J=10.2 Hz, 1H, vinyl-H), 4.69 (d, J=16.8 Hz, 1H, vinyl-H), 4.51 (d, J=10.6 Hz, 1H, C2-H), 4.24 (dd, J=10.6, 2.0 Hz, C2-H), 2.7–2.8 (m, 1H, C4-H), 2.0–2.15 (m, 1H, allylic-H), 1.75–1.9 (m, 1H, allylic-H), 1.28 (s, 3H, C3-CH$_3$).

Starting with the optically active 7-hydroxy-3-(4-hydroxyphenyl)-3-methyl-4-(2-propenyl)chroman prepared in Step 1, a procedure analogous to that as shown in Example 4 or 5 was repeated without protection of hydroxyl groups to give 11-[7-hydroxy-3-(4-hydroxyphenyl)-3-methylchroman-4-yl]-2-(4,4,5,5,5-pentafluoropentyl)undecanoic acid with a cis-configuration having chiral carbons at positions 3 and 4.

$^1$H-NMR (270 MHz, CDCl$_3$): δ 7.08 (d, J=8.6 Hz, 2H, Ar—H), 6.90 (d, J=8.9 Hz, 1H, Ar—H), 6.82 (d, J=8.6 Hz, 2H, Ar—H), 6.3–6.4 (m, 2H, Ar—H), 4.4–5.6 (bs, 2H, OH), 4.51 (d, J=10.2 Hz, 1H, C2-H), 4.24 (dd, J=10.2, 1.3 Hz, 1H, C2-H), 2.55–2.65 (m, 1H, C4-H), 2.35–2.5 (m, 1H, CHCO$_2$H), 1.9–2.2 (m, 2H, CH$_2$CF$_2$), 0.95–1.80 (m, 25H, C3-CH$_3$ and alkyl-H).

Example 8

Synthesis of 11-[7-Hydroxy-3-(4-hydroxyphenyl)-3-methylchroman-4-yl]-2-(4,4,5,5,5-pentafluoropentyl) undecanoic Acid Having Chiral Carbons at Positions 3 and 4

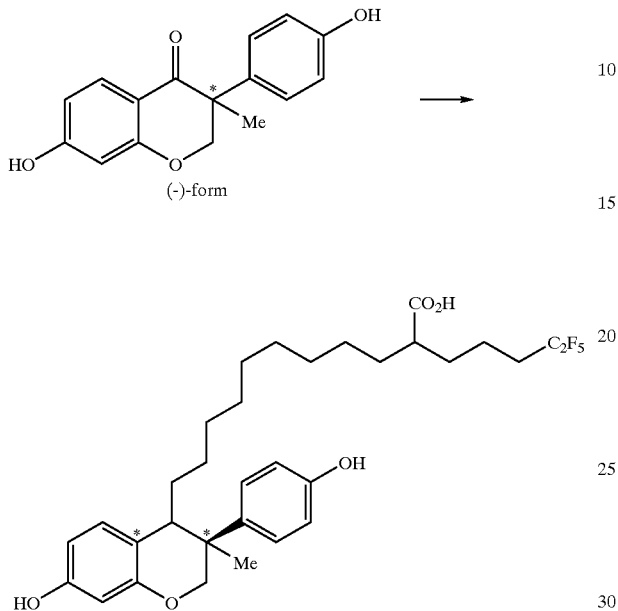

Starting with the (−)-7-hydroxy-3-(4-hydroxyphenyl)-3-methylchroman-4-one prepared in Example 6, a procedure analogous to that as shown in Example 7 was repeated to give 11-[7-hydroxy-3-(4-hydroxyphenyl)-3-methylchroman-4-yl]-2-(4,4,5,5,5-pentafluoropentyl) undecanoic acid with a cis-configuration having chiral carbons at positions 3 and 4.

$^1$H-NMR (270 MHz, CDCl$_3$): δ 7.07 (d, J=9 Hz, 2H, Ar—H), 6.90 (d, J=9 Hz, 1H, Ar—H), 6.82 (d, J=9 Hz, 2H, Ar—H), 6.3–6.4 (m, 2H, Ar—H), 4.51 (d, J=10 Hz, 1H, C2-H), 4.23 (d, J=10 Hz, 1H, C2-H), 2.59 (m, 1H, C4-H), 2.38 (m, 1H, CHCO$_2$H), 1.9–2.2 (m, 2H, CH$_2$CF$_2$), 0.95–1.80 (m, 25H, C3-CH$_3$ and alkyl-H).

Example 9

Synthesis of Optically Active 11-[(3RS,4RS)-7-Hydroxy-3-(4-hydroxyphenyl)-3-methylchroman-4-yl]-2-(4,4,5,5,5-penta-fluoropentyl)undecanoic Acid Having a Chiral Carbon at α-position to the Carboxyl Group (Step 1)

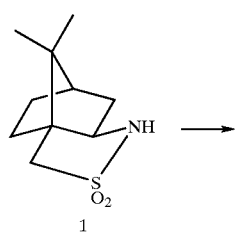

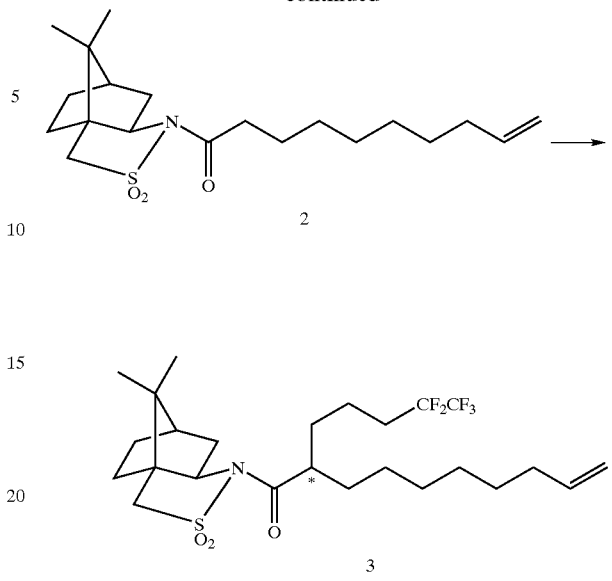

After 60% sodium hydride (480 mg) was washed twice with anhydrous toluene and suspended in anhydrous toluene, a solution of (1S)-(−)-2,10-camphorsultam (1.72 g) in anhydrous toluene (25 ml) was added to the suspension, followed by stirring for 1 hour at room temperature. A solution of 9-decenoylchloride (3.02 g) in anhydrous toluene (25 ml) was further added dropwise to the suspension, followed by stirring for 12 hours at room temperature. Water (30 ml) was added to the reaction mixture, which was then extracted with ethyl acetate. The organic layer was washed with water and saturated aqueous sodium chloride, dried over anhydrous sodium sulfate, and evaporated under reduced pressure to remove the solvent, followed by purification via flash column chromatography to give acylated product 2 (2.08 g, Yield 70%). To a solution of the thus prepared acylated product 2 (368 mg) in tetrahydrofuran (2 ml), a solution of NaHMDS in tetrahydrofuran (1M, 1.0 ml) was added dropwise over 5 minutes while cooling at −78° C., followed by stirring for 1 hour at the same temperature. The reaction mixture was further mixed with 1-iodo-4,4,5,5,5-pentafluoropentane (432 mg) and HMPA (0.522 ml) and then warmed slowly to room temperature. Saturated aqueous chloride was added to the reaction mixture, which was then extracted with ethyl acetate. The organic layer was washed with water and saturated aqueous sodium chloride, dried over anhydrous sodium sulfate, and evaporated under reduced pressure to remove the solvent, followed by purification via flash column chromatography to give alkylated product 3 (297 mg, Yield 56%).

$^1$H-NMR (270 MHz, CDCl$_3$): δ 5.7–5.9 (m, 1H, vinyl), 4.9–5.1 (m, 2H, vinyl), 3.91 (t, 1H, J=6.3 Hz), 3.51 (d, 1H, J=13.9 Hz), 3.43 (d, 1H, J=13.9 Hz), 3.0–3.2 (m, 1H), 0.8–2.2 (m, 25H), 1.14 (s, 3H, Me), 0.97 (s, 3H, Me).

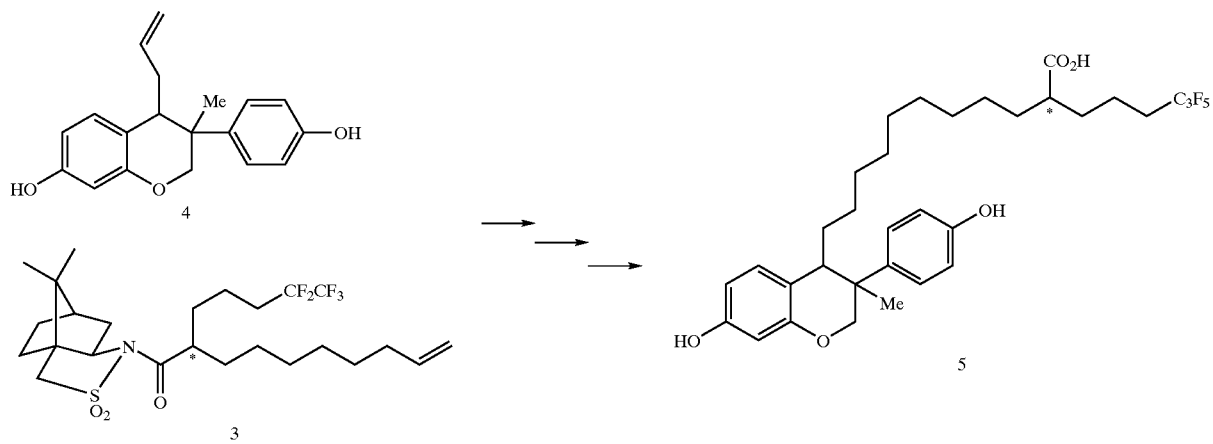

(Step 2)

Starting with the optically active compound 3 prepared in Step 1 (211 mg) and (3RS,4RS)-7-hydroxy-3-(4-hydroxyphenyl)-3-methyl-4-(2-propenyl)chroman 4 (racemate, 59 mg), a procedure analogous to that as shown in Example 7 was repeated to effect metathesis, thereby giving a coupling product (125 mg). This coupling product was subjected to hydrogenation as in Example 7 to give a reduction product (87 mg). To a solution of the reduction product (20 mg) in tetrahydrofuran (0.5 ml), 1M aqueous lithium hydroxide (0.15 ml) was added under nitrogen atmosphere, followed by stirring for 1 day at 50° C. The reaction mixture was acidified by addition of 2N hydrochloric acid, extracted with ethyl acetate, dried over anhydrous magnesium sulfate, and evaporated under reduced pressure to remove the solvent, followed by purification via silica gel column chromatography to give 11-[(3RS,4RS)-7-hydroxy-3-(4-hydroxyphenyl)-3-methylchroman-4-yl]-2-(4,4,5,5,5-pentafluoropentyl)undecanoic acid 5 having a chiral carbon at α-position to the carboxyl group(7.4 mg).

The thus prepared compound 5 was analyzed under the following conditions. Compound 5 was found to give two peaks at retention times of 9.3 and 16.5 minutes, whereas the racemate was found to give four peaks at retention times of 9.3, 10.2, 16.5 and 29.9 minutes.

HPLC analysis conditions: Chiralpak AD (250×4.6 mm ID), hexane/iPrOH/TFA=80/20/0.2, 1.2 ml/min, 206 nm In addition, the corresponding optically active form of racemate 4 can be used in this synthesis to prepare a single isomer compound 5. Although this example illustrates the synthesis of a chroman derivative, a thiochroman derivative can also be prepared in an optically active form by an analogous method.

Example 10

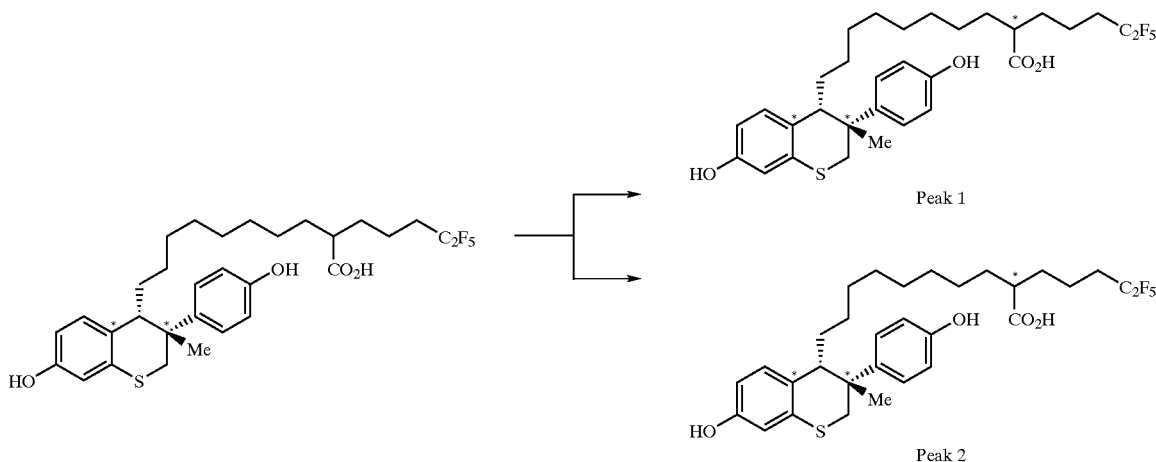

Optical resolution of the 10-[(3R,4R)-7-hydroxy-3-(4-hydroxyphenyl)-3-methylthiochroman-4-yl]-2-(4,4,5,5,5-pentafluoropentyl)decanoic acid prepared in Example 2 was carried out using a chiral column (CHIRALPAK AD) to give optically active isomers, each having chiral carbons at positions 3 and 4 and at α-position to the carboxyl group.

Each isomer provided the same NMR data as shown in Example 2.

Peaks 1 and 2 were detected at retention times of 10.1 and 13.5 minutes, respectively, under the following conditions:
Column used: CHIRALPAK AD (0.46 cm ID×25 cm L)
Mobile phase: hexane/EtOH/acetic acid=85/15/0.1 (v/v/v)

Example 11

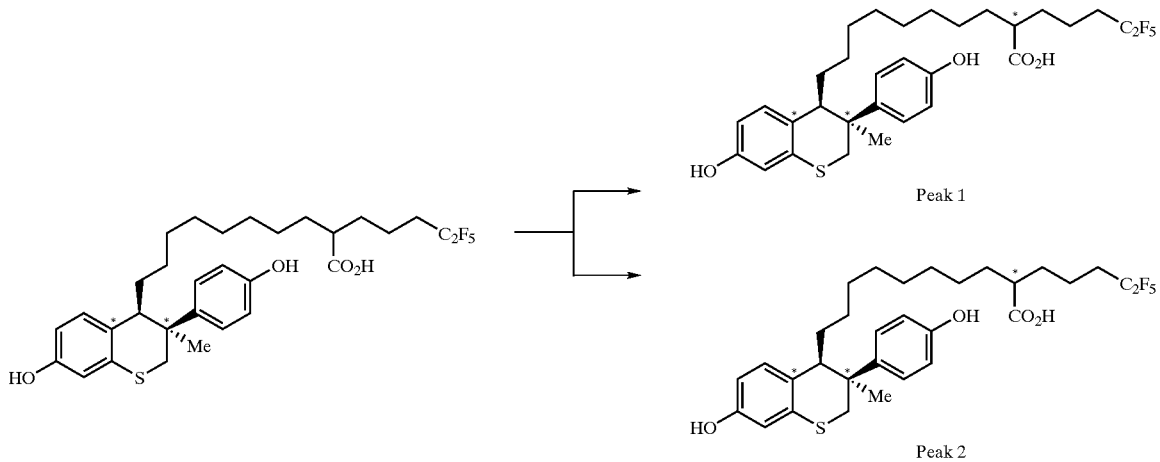

Optical resolution of the 10-[(3S,4S)-7-hydroxy-3-(4-hydroxyphenyl)-3-methylthiochroman-4-yl]-2-(4,4,5,5,5-pentafluoropentyl)decanoic acid prepared in Example 3 was carried out using a chiral column (CHIRALPAK AD) to give optically active isomers, each having chiral carbons at positions 3 and 4 and at α-position to the carboxyl group.

Each isomer provided the same NMR data as shown in Example 3.

Peaks 1 and 2 were detected at retention times of 9.5 and 10.9 minutes, respectively, under the following conditions:

Column used: CHIRALPAK AD (0.46 cm ID×25 cm L)
Mobile phase: hexane/EtOH/acetic acid=85/15/0.1 (v/v/v)
Flow rate: 1.0 ml/min
Column temperature: 40° C.
Detection wavelength: 254 nm

Test Example 1

Anti-estrogenic Activity (Oral Administration)

Test compounds were assayed for their oral anti-estrogenic activity in the following manner. In this experiment, the compounds prepared in Examples 2 and 3 were used as test compounds and the corresponding racemic mixture (10-[(3RS,4RS)-7-hydroxy-3-(4-hydroxyphenyl)-3-methylthiochroman-4-yl]-2-(4,4,5,5,5-pentafluoropentyl) decanoic acid was used as a control compound. This control compound was synthesized according to Reaction Schemes 1 to 7 mentioned above.

To determine anti-estrogenic activity, mice (ICR, weight 30±2 g) which had been ovariectomized 2 weeks before were subcutaneously administered with 17β-estradiol-benzoate (Sigma) in an amount of 0.1 μg/mouse for 3 days and the degree by which the test compound inhibited the increase in uterine weight was measured. In this experiment, each of the test and control compounds was suspended in 5% arabic gum solution and orally administered for 3 days on a once-a-day basis. After 24 hours from the last administration, the test animals were sacrificed and the uteri were removed and weighed. The results obtained are shown in Table 2 below.

TABLE 2

Anti-estrogenic activity in ovariectomized mice administered with 17β-estradiol (oral administration, 3 days)

Test compound/dose (p.o., 3 days)

| Compound | mg/kg | Inhibition (%) |
| --- | --- | --- |
| Example 2 | 10 | 90 |
| Example 3 | 10 | 69 |
| Example 10, Peak 1 | 10 | 87 |
| Example 10, Peak 2 | 10 | 78 |
| 10-[(3RS, 4RS)-7-hydroxy-3-(4-hydroxy-phenyl)-3-methyl-thiochroman-4-yl]-2-(4,4,5,5,5-pentafluoropentyl)decanoic acid | 10 | 75 |

The results shown in Table 2 above indicate that the compounds of the present invention show a superior inhibitory activity against the estradiol-induced increase in uterine weight, as compared to the corresponding racemic mixture.

INDUSTRIAL APPLICABILITY

The compounds of the present invention are highly advantageous in pharmaceutical use because of their anti-estrogenic activity, particularly their superior anti-estrogenic activity over the corresponding racemic mixture.

What is claimed is:

1. A compound having the following general formula (1):

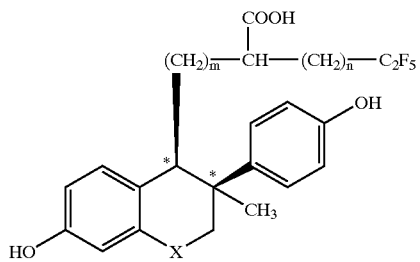

(1)

in which x represents an oxygen atom or a sulfur atom, m represents an integer of 2 to 14, and n represents an integer of 2 to 7, or the following general formula (2):

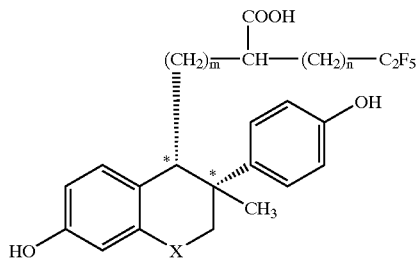

(2)

in which x represents an oxygen atom or a sulfur atom, m represents an integer of 2 to 14, and n represents an integer of 2 to 7, or the following general formula (3):

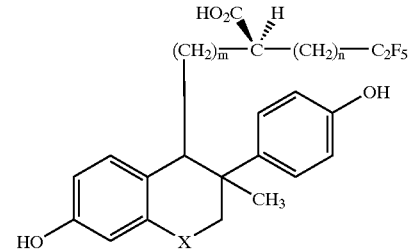

(3)

in which x represents an oxygen atom or a sulfur atom, m represents an integer of 2 to 14, and n represents an integer of 2 to 7, or the following general formula (4):

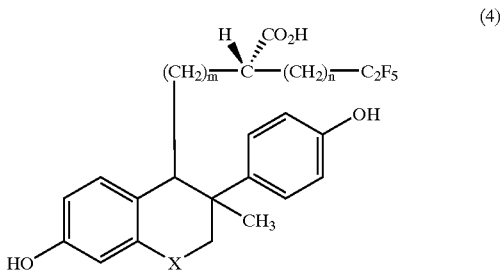

(4)

in which x represents an oxygen atom or a sulfur atom, m represents an integer of 2 to 14, and n represents an integer of 2 to 7, or a hydrate thereof.

2. The compound or hydrate thereof according to claim 1, which has general formula (1), (2), (3) or (4) wherein m is an integer of 6 to 10.

3. The compound or hydrate thereof according to claim 1, which has formula (1), (2), (3) or (4) wherein m is an integer of 8 or 9.

4. The compound or hydrate thereof according to claim 1, which has formula (1), (2), (3) or (4) wherein n is an integer of 3 or 4.

5. The compound or hydrate thereof according to claim 1, which has general formula (1), (2), (3) or (4) wherein X is an oxygen atom or a sulfur atom, m is an integer of 8 or 9, and n is an integer of 3 or 4.

6. The compound or hydrate thereof according to claim 1, which has formula (1) or (2) wherein carbon which is on the side chain bonded to the 4-position of the parent scaffold (i.e., chroman or thiochroman ring) and to which the carboxylic acid in said side chain is bonded has R- or S-configuration or mixtures thereof.

7. The compound or hydrate thereof according to claim 1, which has formula (2).

8. The compound or hydrate thereof according to claim 7, wherein X is a sulfur atom.

9. The compound or hydrate thereof according to claim 1, which has formula (1) or (2) wherein X is an oxygen atom.

10. The compound or hydrate thereof according to claim 1, which is selected from the group consisting of:

10-[(3R,4R)-7-hydroxy-3-(4-hydroxyphenyl)-3-methylthiochroman-4-yl]-(2R)-2-(4,4,5,5,5-pentafluoropentyl)decanoic acid;

10-[(3R,4R)-7-hydroxy-3-(4-hydroxyphenyl)-3-methylthiochroman-4-yl]-(2S)-2-(4,4,5,5,5-pentafluoropentyl)decanoic acid;

10-[(3S,4S)-7-hydroxy-3-(4-hydroxyphenyl)-3-methylthiochroman-4-yl]-(2R)-2-(4,4,5,5,5-pentafluoropentyl)decanoic acid;

10-[(3S,4S)-7-hydroxy-3-(4-hydroxyphenyl)-3-methylthiochroman-4-yl]-(2S)-2-(4,4,5,5,5-pentafluoropentyl)decanoic acid;

10-[(3R,4R)-7-hydroxy-3-(4-hydroxyphenyl)-3-methylthiochroman-4-yl]-2-(4,4,5,5,5-pentafluoropentyl)decanoic acid;

10-[(3S,4S)-7-hydroxy-3-(4-hydroxyphenyl)-3-methylthiochroman-4-yl]-2-(4,4,5,5,5-pentafluoropentyl)decanoic acid;

10-[(3RS,4RS)-7-hydroxy-3-(4-hydroxyphenyl)-3-methylthiochroman-4-yl]-(2R)-2-(4,4,5,5,5-pentafluoropentyl)decanoic acid;

10-[(3RS,4RS)-7-hydroxy-3-(4-hydroxyphenyl)-3-methylthiochroman-4-yl]-(2S)-2-(4,4,5,5,5-pentafluoropentyl)decanoic acid;

11-[(3R,4R)-7-hydroxy-3-(4-hydroxyphenyl)-3-methylthiochroman-4-yl]-(2R)-2-(4,4,5,5,5-pentafluoropentyl)undecanoic acid;

11-[(3R,4R)-7-hydroxy-3-(4-hydroxyphenyl)-3-methylthiochroman-4-yl]-(2S)-2-(4,4,5,5,5-pentafluoropentyl)undecanoic acid;

11-[(3S,4S)-7-hydroxy-3-(4-hydroxyphenyl)-3-methylthiochroman-4-yl]-(2R)-2-(4,4,5,5,,5-pentafluoropentyl)undecanoic acid;

11-[(3S,4S)-7-hydroxy-3-(4-hydroxyphenyl)-3-methylthiochroman-4-yl]-(2S)-2-(4,4,5,5,5-pentafluoropentyl)undecanoic acid;

11-[(3R,4R)-7-hydroxy-3-(4-hydroxyphenyl)-3-methylthiochroman-4-yl]-2-(4,4,5,5,5-pentafluoropentyl)undecanoic acid;

11-[(3S,4S)-7-hydroxy-3-(4-hydroxyphenyl)-3-methylthiochroman-4-yl]-2-(4,4,5,5,5-pentafluoropentyl)undecanoic acid;

11-[(3RS,4RS)-7-hydroxy-3-(4-hydroxyphenyl)-3-methylthiochroman-4-yl]-(2R)-2-(4,4,5,5,5-pentafluoropentyl)undecanoic acid; and 11-[(3RS,4RS)-7-hydroxy-3-(4-hydroxyphenyl)-3-methylthiochroman-4-yl]-(2S)-2-(4,4,5,5,5-pentafluoropentyl)undecanoic acid.

11. A pharmaceutical composition comprising at least one compound or hydrate thereof according to claim 1 as an active ingredient.

12. An anti-estrogenic pharmaceutical composition comprising at least one compound or hydrate thereof according to claim 1 as an active ingredient.

13. A therapeutic agent for breast cancer comprising at least one compound or hydrate thereof according to claim 1 as an active ingredient.

* * * * *